(12) United States Patent
Stutzman-Engwall et al.

(10) Patent No.: US 6,689,611 B1
(45) Date of Patent: *Feb. 10, 2004

(54) MODIFIED STREPTOMYCES HOST CELLS FOR INCREASED AVERMECTIN PRODUCTION AND METHODS OF MAKING THE SAME

(75) Inventors: Kim J. Stutzman-Engwall, East Lyme, CT (US); Brenda S. Price, Antioch, IL (US)

(73) Assignee: Pfizer Inc., New York, NY (US)

(*) Notice: Subject to any disclaimer, the term of this patent is extended or adjusted under 35 U.S.C. 154(b) by 0 days.

This patent is subject to a terminal disclaimer.

(21) Appl. No.: 09/713,893

(22) Filed: Nov. 16, 2000

Related U.S. Application Data

(62) Division of application No. 09/390,721, filed on Sep. 7, 1999, now Pat. No. 6,197,591.
(60) Provisional application No. 60/100,134, filed on Sep. 14, 1998.

(51) Int. Cl.$^7$ ............................................. C12N 15/74

(52) U.S. Cl. ................................... 435/471; 435/76

(58) Field of Search ................... 435/471, 76, 252.35, 435/253.5

(56) References Cited

U.S. PATENT DOCUMENTS

| | | | |
|---|---|---|---|
| 4,362,816 A | 12/1982 | Reusser | 435/172 |
| 4,898,828 A | 2/1990 | Hershberger et al. | 435/252.3 |
| 5,118,617 A | 6/1992 | Ortega et al. | 435/69.1 |
| 5,122,595 A | 6/1992 | Ortega et al. | 530/350 |
| 5,252,474 A | 10/1993 | Gewain et al. | 435/172.3 |
| 5,264,354 A | 11/1993 | Solenberg | 435/172.3 |
| 5,435,730 A | 7/1995 | Adams et al. | 435/69.1 |
| 5,474,912 A | 12/1995 | Sherman et al. | 435/43 |
| 5,525,506 A | 6/1996 | Hafner et al. | 435/253.5 |
| 5,565,359 A | 10/1996 | Hafner et al. | 435/253.5 |
| 5,576,199 A | 11/1996 | Hafner et al. | 435/119 |
| 5,583,015 A | 12/1996 | Hafner et al. | 435/76 |
| 5,583,029 A | 12/1996 | Lam et al. | 435/253.5 |
| 5,707,839 A | 1/1998 | Denoya et al. | 435/119 |
| 5,728,561 A | 3/1998 | Denoya | 435/190 |
| 5,876,987 A | 3/1999 | Champness et al. | 435/172.3 |

FOREIGN PATENT DOCUMENTS

| | | |
|---|---|---|
| EP | 0313297 | 4/1989 |
| EP | 0391594 | 10/1990 |
| WO | 9516781 | 6/1995 |

OTHER PUBLICATIONS

MacNeil et al. Gene, 1992 115, p119–125.
Charter, K. F., 1990, Bio/Technology 8:115–12, "The Improving Prospects for Yield Increase By Genetic Engineering in Antibiotic–Producing Streptomycetes."
Gramajo, H. C. et al., 1993, Molecular Microbiology 7(6):837–845, "Stationary–Phase Production of the Antibiotic Actinorhodin in *Streptomyces Coelicolor* A3(2) is Transcriptionally Regulated."
Bibb, M. J. et al., 1986, Gene 41:357–368, "Cloning and Analysis of the Promoter Region of the Erythromycin–Resistance Gene (ermE) of *Streptomyces Erythraeus*."
Adamidis, T. and Champness, W., 1992, J. Bacteriology 174:4622–4628, "Genetic Analysis of absB, a *Streptomyces Coelicolor* Locus Involved in Global Antibiotic Regulation."
Matsumoto, A. et al., 1994, Gene 146:47–56, "Phosphorylation of the AfsR Protein involved in Secondary Metabolism in Streptomyces Species by a Eukaryotic–Type Protein Kinase."
Parkinson, J. S., and Kofoid, E. C., 1992, Ann. Rev. Gene 26:71–112, "Communication Modules in Bacterial Signaling Proteins."
Laville, J. et al., 1992, Proc. Natl. Acad. Sci, USA 89:1562–1566, "Global Control in *Pseudomonas fluorescens* Mediating Antibiotic Synthesis and Suppression of Black Root Rot of Tobacco."
Dahl, M. K. et al., 1992, J. Biol. Chem. 267:14509–14514, "The Phosphorylation State of the DegU Response Regulator Acts as a Molecular Switch Allowing Either Degradative Enzyme Synthesis or Expression of Genetic Competence in *Bacillus subtilis*."
Stein, D. and Cohen, S. N., 1989, J. Bact. 171:2258–2261, "A Cloned Regulatory Gene of *Streptomyces lividans* Can Supress the Pigment Deficiency Phenotype of Different Developmental Mutants."
Champness, W. C., 1988, J. Bact. 170:1168–1174, "New Loci Required for *Streptomyces coelicolor* Morphological and Physiological Differentiation."
Otten, S. et al., 1995, J. Bact. 177:1216–1224, "Regulation of Daunorubicin Production in *Streptomyces peucetius* by the dnrR$_2$ Locus."
Ishizuka, H. et al., 1992, J. Bact. 174:7585–7594, "A Putative Two–Component Regulatory System Involved in Secondary Metabolism in Streptomyces spp."
Aramidis, T. et al., 1990, J. Bact.172:2962–2969, "Mutations in a New *Streptomyces coelicolor* Locus Which Globally Block Antibiotics Biosynthesis but Not Sporulation."

(List continued on next page.)

Primary Examiner—Ponnathupura Achutamurthy
Assistant Examiner—Kathleen Kerr
(74) Attorney, Agent, or Firm—Peter C. Richardson; Gregg C. Benson; Lance Y. Liu

(57) ABSTRACT

The present invention is directed to compositions and methods for producing avermectins, and is primarily in the field of animal health. The present invention relates to the identification and characterization of two novel genes, herein referred to as the aveR1 and aveR2 genes, that are involved in regulating avermectin polyketide synthase (PKS) expression and avermectin biosynthesis in *Streptomyces avermitilis*. The present invention is based on the discovery that inactivation of these genes results in an increase in the amount of avermectin produced by *S. avermitilis*.

4 Claims, 5 Drawing Sheets

OTHER PUBLICATIONS

Figure 2A:
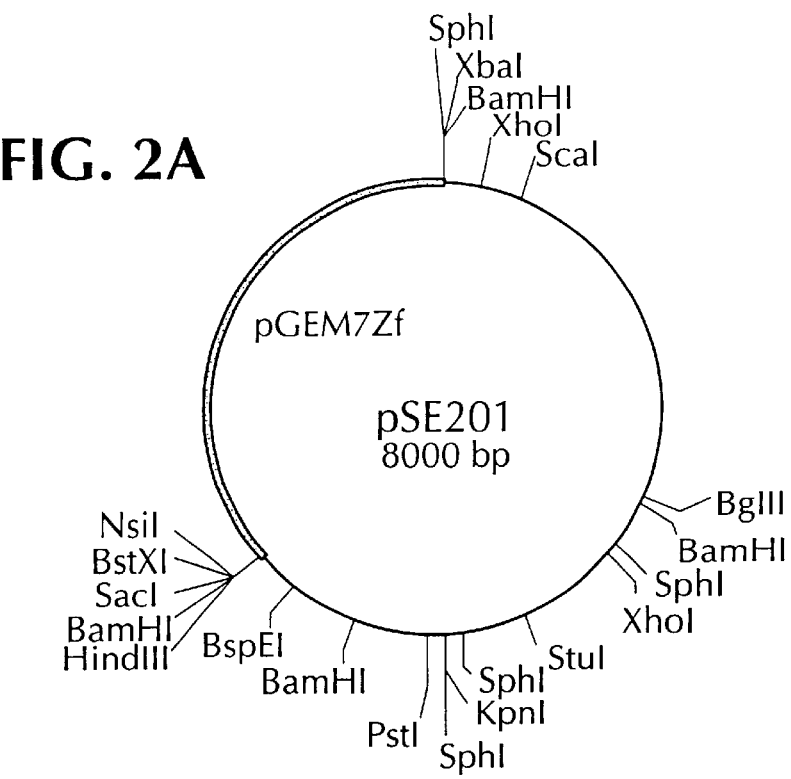

Brian, P. et al., 1996, J. Bact. 178:3221–3231, "Global Negative Regulation of *Streptomyces coelicolor* Antibiotic Synthesis Mediated by an absA–Encoded Putative Signal Transduction System."

Champness, W. et al., 1992, Gene 115:55–60, "Identification of *Streptomyces coelicolor* genes Involved in Regulation of Antibiotic Synthesis."

Fernandez–Moreno, M. A. et al., 1991, Cell 66:769–780, "The act Cluster Contains Regulatory and Antibiotic Export Genes, Direct Targets for Translational Control by the bldA trNA Gene of Streptomyces."

Ikeda et al., 1995, J. Antibiotics 48:532–534, "Construction of a Single Component Producer from the Wild Type Avermectin Producer *Streptomyces avermitilis*."

FIG. 1A

```
aveR1   1 VHAGTAVDPDDHPIL.....ARRLSRRRLIALDGVLVF..AYACALLSTG    43
          :|   ||  .   ..::     .|.:.||   :.|   ||:.   |:|.:  |.|
absA1   1 MHRWQAVRRRIESLVRVLGSERPFTRRADLVLLLVLLVPSAFATGTLET.    49 aveR1  44 PTGISSSSAPPLPAPVPWERLVLIAAATAPVAVRRIWPLPVFAVVLAVTA    93
              |||:    .|:  ||...|.      :.  |:::.::||
absA1  50 .............APVAWLTACLLIAAAVVVQ....RTAPLLSLLLA...    79 aveR1  94 VAVVRDAAWDPFLSAAF..ALYTVAVTVPSRHWWQRWLPGLAIAL.LTVA   140
          |::  . : |:::|.:  .: ||.:..  ::: |::|:   :  |  ..|
absA1  80 .ALL..TLFYPWFGANLWPSMATVVLSCLAGRRLTRLWPAHLVFLCVAAA   126 aveR1 141 GLAGAARAGEAFWWRGSPGLLLLGFAALLGAWQLGRAARQRRAFAVRA..   188
          ||  .|  .|::      ::. :||:  :|.|  :   :|    .||  |:.   :
absA1 127 GLLLVATVGQG...KDWLSLLMTEFVACVLPWWAGNWWSQRTALTHAGWE   173 aveR1 189 .AEQL.......AQRAVTEERLRIARELHDVVTHSMGLIAVKVGVANHVL   230
          ||||        |:.|  .||  |||.::||  :.|.,::::|:   .|.  :   .
absA1 174 HAEQLEWRQRYIADQARMKERARIAQDIHDSLGHELSVMALLAGGLELAP   223 aveR1 231 HIRPQEAYDALQVIERTSRTALNDMRRMLGVLRTSEGERQSAALGPLPGA   280
          :....   .. |:  ||...   |  :  ::::|:||      |  ...:.|.|  .:.
absA1 224 GLSDPHRESVGQLRERCTM.ATERLHEVIGLLR....EDPNPSLTPADES   268 aveR1 281 LA.LPDLVGQAGAQL.....TMRGVESLPDGVALAVYRIVQEALTNVAKH   324
          :|  |.   ....|..:      .  |: .:   |    .||.||:||||||.|||
absA1 269 VAQLVRRFQRSGTPVRFQEDGARDRPGTPLLSDLAAYRVVQEALTNAAKH   318 aveR1 325 AGPEARCRVAVDANGHGVRLEITDDGGDRSPLAPKPG.GHGIVGMRERVA   373
          |  |:..  ||  |.     .:.:.  :.....::   .:|:.  .|  |  |  |:::|  |||
absA1 319 A.PGAPIDVRVTHTADETVVSVVNERPERGGSVPAAGSGSGLIGLDERVR   367 aveR1 374 LYGGTFAAGPRPEGGFAVHASLPYEENT   401
          |  |||:  .|||:  |||.|.|.||   :....
absA1 368 LAGGTLRTGPRA.GGFEVYARLPRGASS   394
```

FIG. 1B

```
absA2    1 .........MIRVLLADDETIIRAGVRSILTTEPGIEVVAEASDGREAV  40
             :|||:|||: ::|  .| :. ||||:   .||.  | |||
aveR2    1 MTRPADPPGAPVRVLIADDQALLRGSLRVLVDTEPGLVATSEAATGTEAV  50 absA2   41 ELARKHRPDVALLDIRMPEMDGLTAAGEM..RTTNPDTAVVVLTTFGEDR  88
           |||.  |||  |:|:|||||||: |   :         |  |.:|| |  |
aveR2   51 RLARQDPPDVVLMDVRMPEMDGIEATRQICGSPETADVKVLILTMFDLDE 100 absA2   89 YIERALDQGVAGFLLKASDPRDLISGVRAVASGGSCLSPLVARRLMTELR 138
           |:   ||   | .|||||  . |  :|:. || :|.|  . |.|  | |||. |
aveR2  101 YVYAALRAGASGFLLKDTPPSELLAAVRVIAAGEALLAPAVTRRLIAEFV 150 absA2  139 RAPSPRSEVSGERTTLLTKREQEVLGMLGAGLSNAEIAQRLHLVEGTIKT 188
             | | |     .|.||.||| ::   |||| |||:||:|    |:||
aveR2  151 HRPEP.SRPLRRTLDGVTEREREVLTLIACGLSNTEIAERLYLGIATVKT 199 absA2  189 YVSAIFTQLEVRNRVQAAIIAYEAGLVKDADLNR*.. 223
           :||  :  |.|   |.| |   |:|||.|||     |
aveR2  200 HVSHLLTKLATRDRAQLVIVAYESGLVTVARPPIGS* 236
```

MODIFIED STREPTOMYCES HOST CELLS FOR INCREASED AVERMECTIN PRODUCTION AND METHODS OF MAKING THE SAME

This application is a divisional of U.S. application Ser. No. 09/390,721, filed Sep. 7, 1999, now U.S. Pat. No. 6,197,591 which claims priority from U.S. provisional application Serial No. 60/100,134 filed Sep. 14, 1998.

1. FIELD OF THE INVENTION

The present invention is directed to compositions and methods for producing avermectins, and is primarily in the field of animal health. More particularly, the present invention relates to the identification and characterization of two novel genes, herein referred to as the aveR1 and aveR2 genes, that are involved in regulating avermectin polyketide synthase (PKS) expression and avermectin biosynthesis in *Streptomyces avermitilis*. The present invention is based on the discovery that inactivation of these genes results in an increase in the amount of avermectin produced by *S. avermitilis*.

2. BACKGROUND OF THE INVENTION

Streptomyces species produce a wide variety of secondary metabolites, including the avermectins, which comprise a series of eight related sixteen-membered macrocyclic lactones with potent anthelmintic and insecticidal activity. The eight distinct but closely related compounds are referred to as A1a, A1b, A2a, A2b, B1a, B1b, B2a, and B2b. The "a" series of compounds refers to the natural avermectin wherein the substituent at the C25 position is (S)-sec-butyl, and the "b" series refers to those wherein the substituent at the C25 position is isopropyl. The designations "A" and "B" refer to avermectins wherein the substituent at C5 is methoxy and hydroxy, respectively. The numeral "1" refers to avermectins wherein a double bond is present at the C22, 23 position, and the numeral "2" refers to avermectins having a hydrogen at the C22 position and a hydroxy at the C23 position. Among the related avermectins, the B1 type of avermectin is recognized as having the most effective antiparasitic and pesticidal activity, and is therefore the most commercially desirable avermectin.

The avermectins and their production by aerobic fermentation of strains of *S. avermitilis* are described, among other places, in U.S. Pat. No. 4,310,519 and 4,429,042.

The avermectin (ave) genes, like many genes involved in the production of secondary metabolites and other Streptomyces antibiotics, are found clustered together on the bacterial chromosome. The ave gene cluster for avermectin biosynthesis spans a 95 kb genomic fragment of DNA which includes DNA encoding the avermectin polyketide synthase (PKS) (MacNeil et al., 1992, Gene 115:119–125).

The regulation of antibiotic biosynthesis in Streptomyces is perhaps best characterized in the species *Streptomyces coelicolor*. Four antibiotics produced by *S. coelicolor* include actinorhodin (Act), undecylprodigiosin (Red), calcium-dependent antibiotic (CDA), and methylenomycin (Mmy). Each of these antibiotics is encoded by a different cluster of genetically distinct genes. Genes have been identified that are linked to either the Act gene cluster or the Red gene cluster that encode products which specifically regulate the expression of the Act biosynthetic gene cluster or the Red biosynthetic gene cluster, respectively. A number of loci containing genes that globally regulate more than one of the antibiotic biosynthetic gene clusters have also been identified. For example, mutations in two independent loci, absA and absB, have been shown to block the synthesis of all four antibiotics in *S. coelicolor* (Brian et al.; 1996, J. Bact. 178:3221–3231). The absA locus has been cloned and characterized, and its gene products have been shown to be involved in a signal transduction pathway which normally acts as a global negative regulator of antibiotic synthesis in *S. coelicolor* (Brian et a., 1996, above).

U.S. Pat. No. 5,876,987 to Champness et al. relates to hyperproduction of antibiotic in Streptomyces spp. as a result of interruption of the absA locus.

U.S. Pat. No. 5,707,839 to Denoya, and U.S. Pat. No. 5,728,561 to Denoya et al. relate to DNA sequences encoding branched-chain alpha-ketoacid dehydrogenase complexes of Streptomyces and methods for enhancing the production of novel avermectins.

Understanding the mechanism by which Type I polyketide synthase expression is regulated in *S. avermitilis* will permit genetic manipulation of the ave genes to increase the production of avermectins.

3. SUMMARY OF THE INVENTION

The present invention provides an isolated polynucleotide molecule comprising a nucleotide sequence encoding an aveR1 gene product from *S. avermitilis*. In a preferred embodiment, the aveR1 gene product comprises the amino acid sequence of SEQ ID NO:2. In a non-limiting embodiment, the isolated polynucleotide molecule of the present invention comprises the nucleotide sequence of the aveR1 ORF of *S. avermitilis* as shown in SEQ ID NO:1 from about nt 1112 to about nt 2317. In a further non-limiting embodiment, the isolated polynucleotide molecule of the present invention comprises the nucleotide sequence of SEQ ID NO:1.

The present invention further provides an isolated polynucleotide molecule that is homologous to a polynucleotide molecule comprising the nucleotide sequence of the aveR1 ORF of *S. avermitilis* as shown in SEQ ID NO:1 from about nt 1112 to about nt 2317.

The present invention further provides an isolated polynucleotide molecule comprising a nucleotide sequence that encodes a polypeptide having an amino acid sequence that is homologous to the amino acid sequence of SEQ ID NO:2.

The present invention further provides an isolated polynucleotide molecule consisting of a nucleotide sequence that is a substantial portion of any of the aforementioned aveR1-related polynucleotide molecules of the present invention. In a preferred embodiment, the substantial portion of the aveR1-related polynucleotide molecule consists of a nucleotide sequence that encodes a peptide fragment of a *S. avermitilis* aveR1 gene product or aveR1-related homologous polypeptide of the present invention. In a specific though non-limiting embodiment, the present invention provides a polynucleotide molecule consisting of a nucleotide sequence encoding a peptide fragment consisting of a subsequence of the amino acid sequence of SEQ ID NO:2.

The present invention further provides an isolated polynucleotide molecule comprising one or more nucleotide sequences that naturally flank the aveR1 ORF of *S. avermitilis* in situ. Such flanking sequences can be selected from the nucleotide sequence of SEQ ID NO:1 from about nt 1 to about nt 1111, and from about nt 2318 to about nt 5045. The present invention further provides an isolated polynucleotide molecule comprising one or more nucleotide sequences that are homologous to nucleotide sequences that naturally flank the aveR1 ORF of *S. avermitilis* in situ. Each flanking sequence, or homolog thereof, in the isolated polynucleotide molecule of the present invention is preferably at least about 200 nt in length. In a non-limiting embodiment, the present invention provides an isolated polynucleotide molecule comprising one or more of the aforementioned nucleotide sequences that naturally flank the aveR1 ORF of S. avermitilis in situ, or that are homologous to such nucleotide sequences, and further comprising one of the aforementioned aveR1-related nucleotide sequences of the present invention such as, e.g., the nucleotide sequence of the aveR1 ORF of S. avermitilis as shown in SEQ ID NO:1 from about nt 1112 to about nt 2317 or substantial portion thereof.

The present invention further provides an isolated polynucleotide molecule comprising a nucleotide sequence encoding an aveR2 gene product from S. avermitilis. In a preferred embodiment, the aveR2 gene product comprises the amino acid sequence of SEQ ID NO:4. In a non-limiting embodiment, the isolated polynucleotide molecule of the present inventon comprises the nucleotide sequence of the aveR2 ORF of S. avermitilis as shown in SEQ ID NO:3 (note: SEQ ID NO:3 is identical to SEQ ID NO:1) from about nt 2314 to about nt 3021. In a further non-limiting embodiment, the isolated polynucleotide molecule of the present invention comprises the nucleotide sequence of SEQ ID NO:3.

The present invention further provides an isolated polynucleotide molecule that is homologous to a polynucleotide molecule comprising the nucleotide sequence of the aveR2 ORF of S. avermitilis as shown in SEQ ID NO:3 from about nt 2314 to about nt 3021.

The present invention further provides an isolated polynucleotide molecule comprising a nucleotide sequence that encodes a polypeptide having an amino acid sequence that is homologous to the amino acid sequence of SEQ ID NO:4.

The present invention further provides an isolated polynucleotide molecule consisting of a nucleotide sequence that is a substantial portion of any of the aforementioned aveR2-related polynucleotide molecules of the present invention. In a preferred embodiment, the substantial portion of the aveR2-related polynucleotide molecule consists of a nucleotide sequence that encodes a peptide fragment of a S. avermitilis aveR2 gene product or aveR2-related homologous polypeptide of the present invention. In a specific though non-limiting embodiment, the present invention provides a polynucleotide molecule consisting of a nucleotide sequence encoding a peptide fragment consisting of a subsequence of the amino acid sequence of SEQ ID NO:4.

The present invention further provides an isolated polynucleotide molecule comprising one or more nucleotide sequences that naturally flank the aveR2 ORF of S. avermitilis in situ. Such flanking sequences can be selected from the nucleotide sequence of SEQ ID NO:3 from about nt 1 to about nt 2313, and from about nt 3022 to about nt 5045. The present invention further provides an isolated polynucleotide molecule comprising one or more nucleotide sequences that are homologous to nucleotide sequences that naturally flank the aveR2 ORF of S. avermitilis in situ. Each flanking sequence in the isolated polynucleotide molecule of the present invention is preferably at least about 200 nt length. In a non-limiting embodiment, the present invention provides an isolated polynucleotide molecule comprising one or more of the aforementioned nucleotide sequences that naturally flank the aveR2 ORF of S. avermitilis in situ, or that are homologous to such nucleotide sequences, and further comprising one of the aforementioned aveR2-related nucleotide sequences of the present invention such as, e.g., the nucleotide sequence of the aveR2 ORF as shown in SEQ ID NO:3 from about nt 2314 to about nt 3021 or a substantial portion thereof.

The present invention further provides an isolated polynucleotide molecule comprising a nucleotide sequence encoding both the aveR1 and aveR2 gene products from S. avermitilis. In a preferred embodiment, the aveR1 and aveR2 gene products comprise the amino acid sequences of SEQ ID NO:2 and SEQ ID NO:4, respectively. In a non-limiting embodiment, the isolated polynucleotide molecule comprises the nucleotide sequence of the aveR1 ORF of S. avermitilis as shown in SEQ ID NO:1 from about nt 1112 to about nt 2317 and the aveR2 ORF of S. avermitilis as shown in SEQ ID NO:1 from about nt 2314 to about nt 021. In a further non-limiting embodiment, the isolated polynucleotide molecule comprises he nucleotide sequence of SEQ ID NO:1 from about nt 1112 to about nt 3021. In a further on-limiting embodiment, the isolated polynucleotide molecule comprises the nucleotide sequence of SEQ ID NO:1.

The present invention further provides an isolated polynucleotide molecule that is homologous to a polynucleotide molecule comprising the nucleotide sequence of both the aveR1 and aveR2 ORFs of S. avermitilis. In a non-limiting embodiment, the present invention provides an isolated polynucleotide molecule that is homologous to a polynucleotide molecule comprising the nucleotide sequence of the aveR1 ORF of S. avermitilis as shown in SEQ ID NO:1 from about nt 1112 to about nt 2317, and the aveR2 ORF of S. avermitilis as shown in SEQ ID NO:1 from about nt 2314 to about nt 3021.

The present invention further provides an isolated polynucleotide molecule comprising a nucleotide sequence that encodes a first polypeptide having an amino acid sequence that is homologous to the amino acid sequence of SEQ ID NO:2 and a second polypeptide having an amino acid sequence that is homologous to the amino acid sequence of SEQ ID NO:4.

The present invention further provides an isolated polynucleotide molecule consisting of a nucleotide sequence that is a substantial portion of any of the aforementioned polynucleotide molecules which comprise a nucleotide sequence encoding both the aveR1 and aveR2 gene products from S. avermitilis or any of the aforementioned polynucleotide molecules that are homologous thereto. In a specific though non-limiting embodiment, the substantial portion of the polynucleotide molecule consists of the nucleotide sequence of the aveR1 ORF as shown in SEQ ID NO:1 from about nt 1112 to about nt 2317. In another specific though non-limiting embodiment, the substantial portion of the polynucleotide molecule consists of the nucleotide sequence of the aveR2 ORF as shown in SEQ ID NO:3 from about nt 2314 to about nt 3021.

The present invention further provides an isolated polynucleotide molecule comprising one or more nucleotide sequences that naturally flank the aveR1 and aveR2 ORFs of S. avermitilis in situ. Such flanking sequences can be selected from the nucleotide sequence of SEQ ID NO:1 from about nt 1 to about nt 1111, and from about nt 3022 to about nt 5045. The present invention further provides an isolated polynucleotide molecule comprising one or more nucleotide sequences that are homologous to nucleotide sequences that naturally flank the aveR1 and aveR2 ORFs of S. avermitilis in situ. Each flanking sequence, or homolog thereof, in the isolated polynucleotide molecule of the present invention is preferably at least about 200 nt in length. In a non-limiting embodiment, the present invention provides an isolated polynucleotide molecule comprising one or more of the aforementioned nucleotide sequences that naturally flank the aveR1 and aveR2 ORFs of *S. avermitilis* in situ, or that are homologoous to such nucleotide sequences, and further comprising one of the aforementioned nucleotide sequences of the present invention that encode either or both of the aveR1 and aveR2 gene products from *S. avermitilis*, such as, e.g., the nucleotide sequence of the aveR1 ORF of *S. avermitilis* as shown in SEQ ID NO:1 from about nt 1112 to about nt 2317, and the nucleotide sequence of the aveR2 ORF of *S. avermitilis* as shown in SEQ ID NO:1 from about nt 2314 to about nt 3021, and substantial portions thereof.

The present invention further provides oligonucleotide molecules that are useful as primers to amplify any of the aforementioned polynucleotide molecules of the present invention or portions thereof, or that can be used to encode or act as anti-sense molecules useful in regulating ave gene expression and avermectin production.

The present invention further provides compositions and methods for cloning and expressing any of the polynucleotide molecules or oligonucleotide molecules of the present invention, including cloning vectors, expression vectors, transformed host cells comprising any of said vectors, and novel strains or cell lines derived therefrom. In a non-limiting embodiment, the present invention provides a recombinant expression vector comprising a polynucleotide molecule of the present invention in operative association with one or more regulatory elements necessary for expression of the polynucleotide molecule. In a specific though non-limiting embodiment, the present invention provides plasmid pSE201 (ATCC 203182), which comprises the complete ORFs of both the aveR1 and aveR2 genes of *S. avermitilis*. Other plasmids are described below.

The present invention further provides a substantially purified or isolated polypeptide encoded by a polynucleotide molecule of the present invention. In a specific though non-limiting embodiment, the polypeptide is an aveR1 gene product comprising the amino acid sequence of SEQ ID NO:2. In another specific though non-limiting embodiment, the polypeptide is an aveR2 gene product comprising the amino acid sequence of SEQ ID NO:4. The present invention further provides substantially purified or isolated polypeptides that are homologous to either the aveR1 or aveR2 gene products of the present invention. The present invention further provides substantially purified or isolated peptide fragments of the aveR1 or aveR2 gene products or homologous polypeptides of the present invention.

The present invention further provides a method of preparing a substantially purified or isolated aveR1 gene product, aveR2 gene product, homologous polypeptide, or peptide fragment of the present invention, comprising culturing a host cell transformed or transfected with a recombinant expression vector of the present invention under conditions conducive to the expression of the particular encoded gene product, polypeptide, or peptide fragment, and recovering the expressed gene product, polypeptide, or peptide fragment from the cell culture.

The present invention further provides compositions and methods for genetically modifying the cells of a species or strain of Streptomyces, including genetic constructs such as, e.g., gene replacement vectors. As provided by the present invention, the cells of a species or strain of Streptomyces are genetically modified to produce an amount of avermectins which is detectably different from the amount of avermectins produced by cells of the same species or strain that have not been so modified. In a preferred embodiment, the cells of a species or strain of Streptomyces are genetically modified to produce a detectably increased amount of avermectins compared to the amount of avermectins produced by cells of the same species or strain that have not been so modified. In a further preferred embodiment, the species of Streptomyces is *S. avermitilis*. According to the present invention, such genetic modification preferably comprises mutating either an aveR1 homolog gene, or an aveR2 homolog gene, or both the aveR1 and aveR2 homolog genes, where such mutation results in a detectable increase in the amount of avermectins produced by cells of a strain of Streptomyces carrying the mutation compared to cells of the same strain that do not carry the gene mutation. Mutation of either the aveR1 homolog gene or the aveR2 homolog gene, or both aveR1 and aveR2 homolog genes, can be carried out using standard mutagenic techniques, including exposure to a chemical mutagen or radiation, or by using a genetic construct provided by the present invention, such as, e.g., a gene replacement vector, to mutate the aveR1 homolog gene or aveR2 homolog gene, or both aveR1 and aveR2 homolog genes, by, e.g., adding, deleting or substituting nucleotides, or by introducing a frame-shift, or by inserting a different or heterologous nucleotide sequence into the aveR1 homolog gene or aveR2 homolog gene, or by deleting a portion or all of either the aveR1 homolog gene or the aveR2 homolog gene, or both the aveR1 and aveR2 homolog genes, or by replacing a portion or all of either the aveR1 homolog gene or the aveR2 homolog gene, or both the aveR1 and aveR2 homolog genes, with a different or heterologous nucleotide sequence, or by a combination of such mutations.

The present invention further provides a method for identifying a mutation of an aveR1 homolog gene or aveR2 homolog gene, or of both aveR1 and aveR2 homolog genes, in a species or strain of Streptomyces, which mutation is capable of detectably increasing the amount of avermectins produced by cells of the species or strain of Streptomyces carrying the gene mutation compared to cells of the same species or strain of Streptomyces that do not carry the gene mutation, comprising: (a) measuring the amount of avermectins produced by cells of the particular species or strain of Streptomyces;. (b) introducing a mutation into the aveR1 homolog gene or aveR2 homolog gene, or into both the aveR1 and aveR2 homolog genes, of cells of the species or strain; and (c) comparing the amount of avermectins produced by the cells carrying the gene mutation as produced in step (b) to the amount of avermectins produced by the cells of step (a) that do not carry the gene mutation; such that if the amount of avermectins produced by the cells carrying the gene mutation as produced in step (b) is detectably higher than the amount of avermectins produced by the cells of step (a) that do not carry the gene mutation, then a mutation of the aveR1 or aveR2 homolog gene, or of both the aveR1 and aveR2 homolog genes, capable of detectably increasing the amount of avermectins has been identified. In a preferred embodiment, the species of Streptomyces is *S. avermitilis*.

The present invention further provides a method of preparing genetically modified cells from a particular species or strain of Streptomyces, which modified cells produce a detectably increased amount of avermectins compared to unmodified cells of the species or strain, comprising mutating the aveR1 homolog gene or the aveR2 homolog gene, or both the aveR1 and aveR2 homolog genes, in cells of the species or strain of Streptomyces, and selecting those cells which produce a detectably increased amount of avermectins as a result of the mutation compared to cells of the same species or strain of Streptomyces that do not carry the gene mutation. In a preferred embodiment, the species of Streptomyces is S. avermitilis. In a specific though non-limiting embodiment described below in Section 6.9.1, both the aveR1 and aveR2 genes of S. avermitilis were mutated by replacing a portion of the ORF of each gene with a heterologous gene, resulting in S. avermitilis cells that produce a detectably increased amount of avermectins compared to cells of the same strain of S. avermitilis in which the aveR1 and aveR2 genes have not been so mutated. In another specific though non-limiting embodiment described below in Section 6.9.2, the aveR2 gene of S. avermitilis was mutated by inserting a heterologous gene into the aveR2 ORF, resulting in S. avermitilis cells that produce a detectably increased amount of avermectins compared to cells of the same strain of S. avermitilis in which the aveR2 gene has not been so mutated.

The present invention further provides novel strains of Streptomyces, the cells of which produce a detectably increased amount of avermectins as a result of one or more mutations to the aveR1 homolog gene or aveR2 homolog gene, or to both the aveR1 and aveR2 homolog genes, compared to cells of the same strain of Streptomyces that do not carry the gene mutation. In a preferred embodiment, the strain of Streptomyces is from the species S. avermitilis. The novel strains of the present invention are useful in the large-scale production of avermectins, such as the commercially desirable doramectin.

The present invention further provides a process for increasing the amount of avermectins produced by cultures of Streptomyces, comprising culturing cells of a particular species or strain of Streptomyces, which cells comprise a mutation in the aveR1 homolog gene or aveR2 homolog gene, or in both the aveR1 and aveR2 homolog genes, and which gene mutation serves to detectably increase the amount of avermectins produced by cells of the species or strain of Streptomyces carrying the gene mutation compared to cells of the same species or strain that do not carry the gene mutation, in culture media under conditions which permit or induce the production of avermectins therefrom, and recovering the avermectins from the culture. In a preferred embodiment, the species of Streptomyces is S. avermitilis. This process is useful to increase the production efficiency of avermectins.

The present invention further provides antibodies directed against an aveR1 gene product, aveR2 gene product, homologous polypeptide, or peptide fragment of the present invention.

4. BRIEF DESCRIPTION OF THE FIGS.

FIG. 1. A. Comparison of deduced amino acid sequences encoded by the S. coelicolor histidine kinase absA1 locus (SEQ ID NO:5) and the S. avermitilis aveR1 gene (SEQ ID NO:2) indicates about 32% sequence identity. B. Comparison of deduced amino acid sequences encoded by the S. coelicolor response regulator absA2 locus (SEQ ID NO:6) and the S. avermitilis aveR2 gene (SEQ ID NO:4) indicates about 45% sequence identity. Highly conserved amino acids are in bold-face type.

FIG. 2. A. Plasmid vector pSE201 (ATCC 203182) containing the aveR1 and aveR2 ORFs. B. Plasmid vector pSE210 containing the aveR1 and aveR2 ORFs.

Figure 3A:
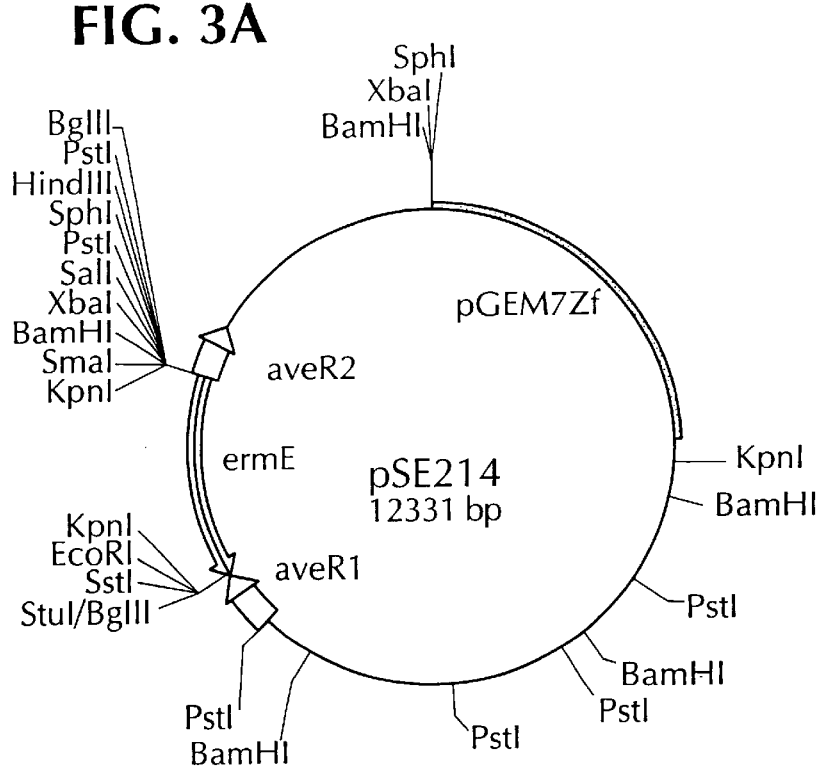
Figure 3B:
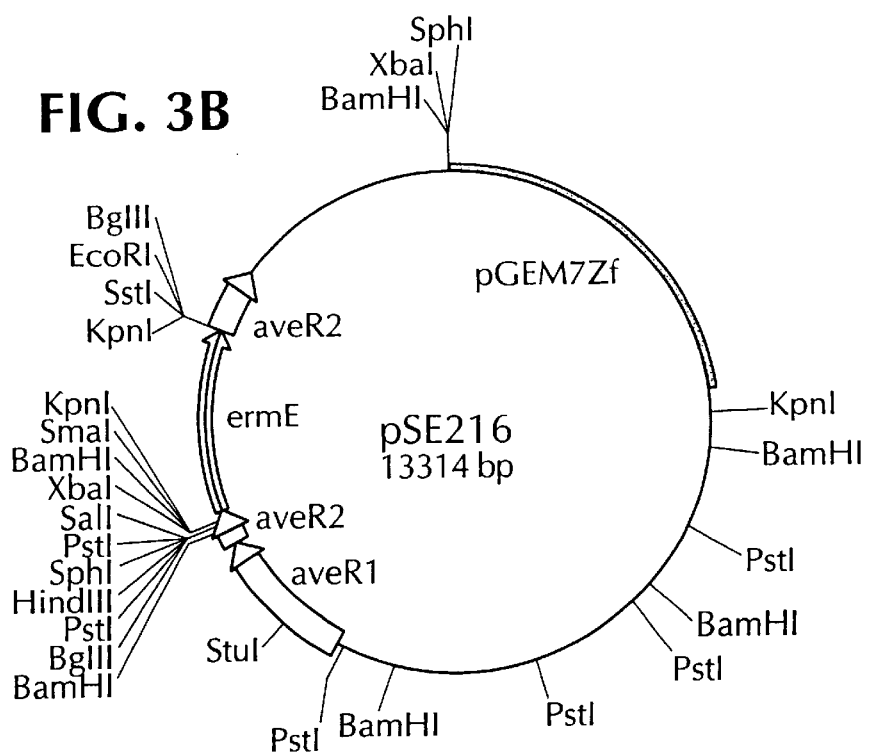

FIG. 3. A. Gene replacement vector pSE214 containing the ermE gene, which has replaced a portion of the aveR1 and aveR2 ORFs. B. Gene replacement vector pSE216 containing the ermE gene inserted into the aveR2 ORF.

Figure 4:
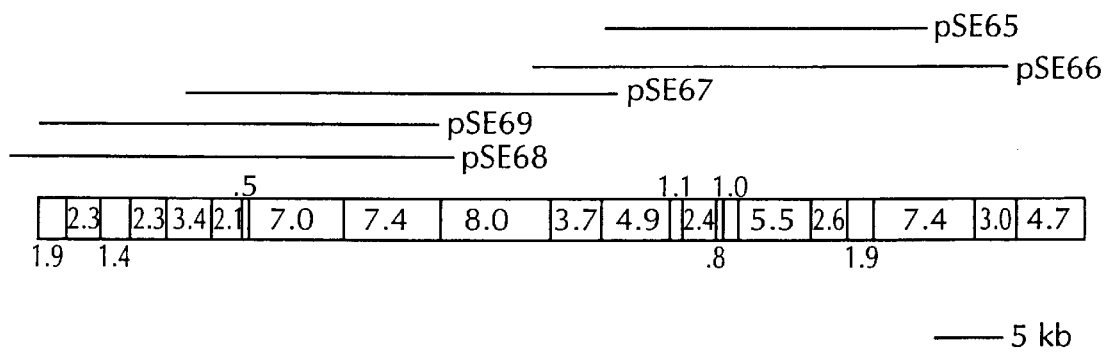

FIG. 4. BamHI restriction map of the avermectin polyketide synthase gene cluster from S. avermitilis with five overlapping cosmid clones identified (i.e., pSE65, pSE66, pSE67, pSE68, pSE69).

5. DETAILED DESCRIPTION OF THE INVENTION

The present invention relates to the identification and characterization of polynucleotide molecules having nucleotide sequences that encode the aveR1 and aveR2 gene products from S. avermitilis, and the discovery that mutation of these genes can modulate the amount of avermectins produced. By way of example, the invention is described in the sections below for a polynucleotide molecule comprising the nucleotide sequence of the aveR1 ORF as shown in SEQ ID NO:1 from about nt 1112 to about nt 2317, or as present in plasmid pSE201 (ATCC 203182), and for a polynucleotide molecule comprising the nucleotide sequence of the aveR2 ORF as shown in SEQ ID NO:3 (note: SEQ ID NO:3 is identical to SEQ ID NO:1) from about nt 2314 to about nt 3021, or as present in plasmid pSE201 (ATCC 203182), and for polynucleotides molecules comprising mutated nucleotide sequences derived therefrom. References herein to the nucleotide sequences shown in SEQ ID NOS:1 and 3, and to substantial portions thereof, are intended to also refer to the corresponding nucleotide sequences and substantial portions thereof, respectively, as present in plasmid pSE201 (ATCC 203182), unless otherwise indicated. In addition, references herein to the amino acid sequences shown in SEQ ID NOS:2 and 4, and to peptide fragments thereof, are intended to also refer to the corresponding amino acid sequences and peptide fragments thereof, respectively, encoded by the corresponding AveR1- and AveR2-encoding nucleotide sequences present in plasmid pSE201 (ATCC 203182), unless otherwise indicated.

5.1. Polynucleotide Molecules

As used herein, the terms "polynucleotide molecule," "polynucleotide sequence," "coding sequence," "open-reading frame (ORF)", and the like, are intended to refer to both DNA and RNA molecules, which can either be single-stranded or double-stranded. A coding sequence or ORF can include but is not limited to prokaryotic sequences, cDNA sequences, genomic DNA sequences, and chemically synthesized DNA and RNA sequences.

Production and manipulation of the polynucleotide molecules and oligonucleotide molecules disclosed herein are within the skill in the art and can be carried out according to recombinant techniques described, among other places, in Maniatis et al. 1989, *Molecular Cloning, A Laboratory Manual*, Cold Spring Harbor Laboratory Press, Cold Spring Harbor, N.Y.; Ausubel et al., 1989, *Current Protocols in Molecular Biology*, Greene Publishing Associates & Wiley Interscience, N.Y.; Sambrook et al., 1989, *Molecular Cloning: A Laboratory Manual*, 2d ed., Cold Spring Harbor Laboratory Press, Cold Spring Harbor, N.Y.; Innis et al. (eds), 1995, *PCR Strategies*, Academic Press, Inc., San Diego; Erlich (ed), 1992, *PCR Technology*, Oxford University Press, New York; and Hopwood et al., 1985, *Genetic Manipulation of Streptomyces, A Laboratory Manual*, John Innes Foundation, Norwich, U. K., all of which are incorporated herein by reference.

5.1.1. aveR1 -Related Polynucleotide Molecules

The present invention provides an isolated polynucleotide molecule comprising a nucleotide sequence encoding an aveR1 gene product from S. avermitilis. In a preferred embodiment, the aveR1 gene product comprises the amino acid sequence of SEQ ID NO:2. In a non-limiting embodiment, the isolated polynucleotide molecule of the present invention comprises the nucleotide sequence of the aveR1 ORF of S. avermitilis as shown in SEQ ID NO:1 from about nt 1112 to about nt 2317. In a further non-limiting embodiment, the isolated polynucleotide molecule of the present invention comprises the nucleotide sequence of SEQ ID NO:1.

The present invention further provides an isolated polynucleotide molecule that is homologous to a polynucleotide molecule comprising the nucleotide sequence of the aveR1 ORF of S. avermitilis as shown in SEQ ID NO:1 from about nt 1112 to about nt 2317. The term "homologous" when used in this respect means a polynucleotide molecule comprising a nucleotide sequence: (a) that encodes the same polypeptide as SEQ ID NO:1 from about nt 1112 to about nt 2317, but that includes one or more silent changes to the nucleotide sequence according to the degeneracy of the genetic code; or (b) that hybridizes to the complement of a polynucleotide molecule comprising a nucleotide sequence that encodes a polypeptide comprising the amino acid sequence of SEQ ID NO:2 under moderately stringent conditions, i.e., hybridization to filter-bound DNA in 0.5 M $NaHPO_4$, 7% sodium dodecyl sulfate (SDS), 1 mM EDTA at 65° C., and washing in 0.2×SSC/0.1% SDS at 42° C. (see Ausubel et aL. (eds.), 1989, Current Protocols in Molecular Biology, Vol. I, Green Publishing Associates, Inc., and John Wiley & Sons, Inc., New York, at p. 2.10.3), and is useful in practicing the invention. In a preferred embodiment, the homologous polynucleotide molecule hybridizes to the complement of a polynucleotide molecule comprising a nucleotide sequence that encodes a polypeptide comprising the amino acid sequence of SEQ ID NO:2 under highly stringent conditions, i.e., hybridization to filter-bound DNA in 0.5 M $NaHPO_4$, 7% SDS, 1 mM EDTA at 65° C., and washing in 0.1×SSC/0.1% SDS at 68° C. (Ausubel et aL, 1989, above), and is useful in practicing the invention. In a further preferred embodiment, the homologous polynucleotide molecule hybridizes under highly stringent conditions to the complement of a polynucleotide molecule comprising the nucleotide sequence of SEQ ID NO:1 from about nt 1112 to about nt 2317, and is useful in practicing the invention. In a further preferred embodiment, the homologous polynucleotide molecule has a nucleotide sequence having at least about 70%, more preferably at least about 80%, and most preferably at least about 90% sequence identity to the nucleotide sequence of SEQ ID NO: 1 from about nt 1112 to about nt 2317, as determined by any standard nucleotide sequence identity algorithm, such as BLASTN (GENBANK, NCBI), and hybridizes under highly stringent conditions to the complement of such a polynucleotide molecule, and is useful in practicing the invention.

As used herein, an aveR1-related polynucleotide molecule is "useful in practicing the invention" where the polynucleotide molecule can be used to introduce mutations into the aveR1 ORF of S. avermitilis by site-directed mutagenesis, such as by homologous recombination, or to amplify a polynucleotide molecule comprising the nucleotide sequence of the aveR1 ORF of S. avermitilis using standard amplification techniques. Such homologous polynucleotide molecules can include naturally occurring aveR1 homolog genes present in other species of Streptomyces or in other strains of S. avermitilis, as well as mutated aveR1 alleles, whether naturally occurring, chemically synthesized, or genetically engineered.

The present invention further provides an isolated polynucleotide molecule comprising a nucleotide sequence that encodes a polypeptide having an amino acid sequence that is homologous to the amino acid sequence of SEQ ID NO:2. As used herein to refer to polypeptides having amino acid sequences that are homologous to the amino acid sequence of an aveR1 gene product from S. avermitilis, the term "homologous" means a polypeptide comprising the amino acid sequence of SEQ ID NO:2, but in which one or more amino acid residues thereof has been conservatively substituted with a different amino acid residue, where the resulting polypeptide is useful in practicing the invention. Conservative amino acid substitutions are well-known in the art. Rules for making such substitutions include those described by Dayhof, M. D., 1978, Nat. Biomed. Res. Found., Washington, D.C., Vol. 5, Sup. 3, among others. More specifically, conservative amino acid substitutions are those that generally take place within a family of amino acids that are related in the acidity or polarity of their side chains. Genetically encoded amino acids are generally divided into four groups: (1) acidic=aspartate, glutamate; (2) basic= lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. One or more replacements within any particular group, e.g., of a leucine with an isoleucine or valine, or of an aspartate with a glutamate, or of a threonine with a serine, or of any other amino acid residue with a structurally related amino acid residue, e.g., an amino acid residue with similar acidity or polarity, or with similarity in some combination thereof, will generally have an insignificant effect on the function of the polypeptide. In a preferred embodiment, the homologous polypeptide has at least about 70%, more preferably at least about 80%, and most preferably at least about 90% amino acid sequence identity to the amino acid sequence of SEQ ID NO:2, as determined by any standard amino acid sequence identity algorithm, such as BLASTP (GENBANK, NCBI).

As used herein, an aveR1-related polypeptide is "useful in practicing the invention" where the polypeptide can be used to raise antibodies against an aveR1 gene product from S. avermitilis, or to screen for compounds that modulate AveR1 activity or avermectin production in Streptomyces.

The present invention further provides an isolated polynucleotide molecule consisting of a nucleotide sequence that is a substantial portion of any of the aforementioned aveR1-related polynucleotide molecules of the present invention. As used herein, a "substantial portion" of an aveR1-related polynucleotide molecule means a polynucleotide molecule consisting of less than the complete coding sequence of a S. avermitilis aveR1 gene product or aveR1-related homologous polypeptide of the present invention, but comprising at least about 20%, and more preferably at least about 30%, of said nucleotide sequence, and that is useful in practicing the invention, as usefulness is defined above for aveR1-related polynucleotide molecules.

In a non-limiting embodiment, the substantial portion of the aveR1-related polynucleotide molecule consists of a nucleotide sequence that encodes a peptide fragment of a S. avermitilis aveR1 gene product or aveR1-related homologous polypeptide of the present invention. A "peptide fragment" of an aveR1-related polypeptide refers to a polypeptide consisting of a sub-sequence of the amino acid sequence of a full-length aveR1 gene product or homologous polypeptide, which sub-sequence is shorter in length than the full-length aveR1 gene product or homologous polypeptide, and which sub-sequence is useful in practicing the invention, as usefulness is defined above for aveR1-related polypeptides. In a preferred embodiment, the present invention provides a polynucleotide molecule consisting of a nucleotide sequence encoding a peptide fragment consisting of a sub-sequence of the amino acid sequence of SEQ ID NO:2. Peptide fragments of the invention are preferably at least about 15 amino acid residues in length.

The aveR1 -related polynucleotide molecules disclosed herein can be used to express the aveR1 gene product, to prepare novel strains of Streptomyces in which the aveR1 gene has been mutated, and to identify aveR1 homolog genes in other bacterial species or strains using known techniques. Thus, the present invention further provides an isolated polynucleotide molecule comprising a nucleotide sequence encoding an aveR1 homolog gene product. As used herein, an "aveR1 homolog gene product" is defined as a gene product encoded by an aveR1 homolog gene which, in turn, is defined in relation to the aveR1 gene of S. avermitilis as a gene from a different species of Streptornyces or the closely related Saccharopolyspora genus and which is recognized by those of skill in the art as a homolog of the aveR1 gene of S. avermitilis based on a degree of nucleotide sequence identity greater than about 80%, and which also contains the conserved active site residues typically found in histidine kinase components of two-component signaling systems, and which is also closely linked to the regulated antibiotic biosynthetic genes. For example, aveR1 homology comparisons with eubacterial two-component systems from the Nar/Deg subgroups show 100% conservation of the histidine residue (H) which is the site of auto-phosphorylation, and the asparagine residue (N) which is required for autokinase activity. As used herein, the term "aveR1 homolog gene" includes the S. avermitilis aveR1 gene itself.

Methods for identifying polynucleotide clones containing aveR1 homolog genes are known in the art. For example, a polynucleotide molecule comprising a portion of the S. avermitilis aveR1 ORF can be detectably labeled and used to screen a genomic library constructed from DNA derived from the organism of interest. The stringency of the hybridization conditions can be selected based on the relationship of the reference organism, in this example S. avermitilis, to the organism of interest. Requirements for different stringency conditions are well known to those of skill in the art, and such conditions will vary predictably depending on the specific organisms from which the library and the labeled sequences are derived. Genomic DNA libraries can be screened for aveR1 homolog gene coding sequences using the techniques set forth, among other places, in Benton and Davis, 1977, Science 196:180, for bacteriophage libraries, and in Grunstein and Hogness, 1975, Proc. Nati. Acad. Sci. USA, 72:3961–3965, for plasmid libraries, which publications are incorporated herein by reference. Polynucleotide molecules having nucleotide sequences known to include the aveR1 ORF, as shown in SEQ ID NO:1, or oligonucleotide molecules representing portions thereof, can be used as probes in these screening experiments. Alternatively, oligonucleotide probes can be synthesized that correspond to nucleotide sequences deduced from the amino acid sequence of the purified aveR1 homolog gene product.

Clones identified as containing aveR1 homolog gene coding sequences can be tested for appropriate biological function. For example, the clones can be subjected to sequence analysis in order to identify a suitable reading frame, as well as initiation and termination signals. The cloned DNA sequence can then be inserted into an appropriate expression vector which is then transformed into cells of a strain of S. avermitilis that have been rendered aveR1 ⁻ to test for complementation. Transformed S. avermitilis host cells can then be analyzed for avermectin production using methods such as HPLC analysis of fermentation products, as described, e.g., in Section 6.6, below.

The present invention further provides an isolated polynucleotide molecule comprising one or more nucleotide sequences that naturally flank the aveR1 ORF of S. avermitilis in situ. Such flanking sequences can be selected from the nucleotide sequence of SEQ ID NO:1 from about nt 1 to about nt 1111, and from about nt 2318 to about nt 5045. The present invention further provides an isolated polynucleotide molecule comprising one or more nucleotide sequences that are homologous to nucleotide sequences that naturally flank the aveR1 ORF of S. avermitilis in situ. As used herein, a nucleotide sequence is homologous to a nucleotide sequence which naturally flanks the aveR1 ORF of S. avermitilis in situ where the homologous nucleotide sequence hybridizes to the complement of the nucleotide sequence which naturally flanks the aveR1 ORF of S. avermitilis in situ under moderately stringent conditions, i.e., hybridization to filter-bound DNA in 0.5 M $NaHPO_4$, 7% SDS, 1 mM EDTA at 65° C., and washing in 0.2×SSC/0.1% SDS at 42° C. (see Ausubel et al., 1989, above), and is useful in practicing the invention, as usefulness is defined above for aveR1-related polynucleotide molecules. Each flanking sequence, or homolog thereof, in the isolated polynucleotide molecule of the present invention is preferably at least about 200 nt in length. In a non-limiting embodiment, the present invention provides an isolated polynucleotide molecule comprising one or more of the aforementioned nucleotide sequences that naturally flank the aveR1 ORF of S. avermitilis in situ, or that are homologous to such nucleotide sequences, and further comprising one of the aforementioned aveR1-related nucleotide sequences of the present invention such as, e.g., the nucleotide sequence of the aveR1 ORF of S. avermitilis as shown in SEQ ID NO:1 from about nt 1112 to about nt 2317 or a substantial portion thereof.

5.1.2. aveR2-Related Polynucleotide Molecules

The present invention further provides an isolated polynucleotide molecule comprising a nucleotide sequence encoding an aveR2 gene product from S. avermitilis. In a preferred embodiment, the aveR2 gene product comprises the amino acid sequence of SEQ ID NO:4. In a non-limiting embodiment, the isolated polynucleotide molecule of the present invention comprises the nucleotide sequence of the aveR2 ORF of S. avermitilis as shown in SEQ ID NO:3 from about nt 2314 to about nt 3021. In a further non-limiting embodiment, the isolated polynucleotide molecule of the present invention comprises the nucleotide sequence of SEQ ID NO:3.

The present invention further provides an isolated polynucleotide molecule that is homologous to a polynucleotide molecule comprising the nucleotide sequence of the aveR2 ORF of S. avermitilis as shown in SEQ ID NO:3 from about nt 2314 to about nt 3021. The term "homologous" when used in this respect means a polynucleotide molecule comprising a nucleotide sequence: (a) that encodes the same polypeptide as SEQ ID NO:3 from about nt 2314 to about nt 3021, but that includes one or more silent changes to the nucleotide sequence according to the degeneracy of the genetic code; or (b) that hybridizes to the complement of a polynucleotide molecule comprising a nucleotide sequence that encodes a polypeptide comprising the amino acid sequence of SEQ ID NO:4 under moderately stringent conditions, i.e., hybridization to filter-bound DNA in 0.5 M $NaHPO_4$, 7% SDS, 1 mM EDTA at 65° C., and washing in 0.2×SSC/0.1% SDS at 42° C. (Ausubel et al., 1989, above), and is useful in practicing the invention. In a preferred embodiment, the homologous polynucleotide molecule hybridizes to the complement of a polynucleotide molecule comprising a nucleotide sequence that encodes a polypeptide comprising the amino acid sequence of SEQ ID NO:4 under highly stringent conditions, i.e., hybridization to filter-bound DNA in 0.5 M NaHPO$_4$, 7% SDS, 1 mM EDTA at 65° C., and washing in 0.1×SSC/0.1 % SDS at 68° C. (Ausubel et al., 1989 above), and is useful in practicing the invention. In a further preferred embodiment, the homologous polynucleotide molecule hybridizes under highly stringent conditions to the complement of a polynucleotide molecule comprising the nucleotide sequence of SEQ ID NO:3 from about nt 2314 to about nt 3021, and is useful in practicing the invention. In a further preferred embodiment, the homologous polynucleotide molecule has a nucleotide sequence having at least about 70%, more preferably at least about 80%, and most preferably at least about 90% sequence identity to the nucleotide sequence of SEQ ID NO:3 from about nt 2314 to about nt 3021, as determined by any standard nucleotide sequence identity algorithm, such as BLASTN (GENBANK, NCBI), and hybridizes under highly stringent conditions to the complement of such a polynucleotide molecule, and is useful in practicing the invention.

As used herein, an aveR2-related polynucleotide molecule is "useful in practicing the invention" where the polynucleotide molecule can be used to introduce mutations into the aveR2 ORF by site-directed mutagenesis, such as by homologous recombination, or to amplify a polynucleotide molecule comprising the nucleotide sequence of the aveR2 ORF of *S. avermitilis* using standard amplification techniques. Such homologous polynucleotide molecules can include naturally occurring aveR2 genes present in other species of S&reptomyces or in other strains of *S. avermitilis*, as well as mutated aveR2 alleles, whether naturally occurring, chemically synthesized, or genetically engineered.

The present invention further provides an isolated polynucleotide molecule comprising a nucleotide sequence that encodes a polypeptide having an amino acid sequence that is homologous to the amino acid sequence of SEQ ID NO:4. As used herein to refer to polypeptides having amino acid sequences that are homologous to the amino acid sequence of an aveR2 gene product from *S. avermitilis*, the term "homologous" means a polypeptide comprising the amino acid sequence of SEQ ID NO:4, but in which one or more amino acid residues thereof has been conservatively substituted with a different amino acid residue, as conservative amino acid substitutions are defined above, where the resulting polypeptide is useful in practicing the invention. In a preferred embodiment, the homologous polypeptide has at least about 70%, more preferably at least about 80%, and most preferably at least about 90% amino acid sequence identity to the amino acid sequence of SEQ ID NO:4, as determined by any standard amino acid sequence identity algorithm, such as BLASTP (GENBANK, NCBI).

As used herein, an aveR2-related polypeptide is "useful in practicing the invention" where the polypeptide can be used to raise antibodies against an aveR2 gene product from *S. avermitilis*, or to screen for compounds that modulate AveR2 activity or avermectin production in Streptomyces.

The present invention further provides an isolated polynucleotide molecule consisting of a nucleotide sequence that is a substantial portion of any of the aforementioned aveR2-related polynucleotide molecules of the present invention.

As used herein, a "substantial portion" of an aveR2-related polynucleotide molecule means a polynucleotide molecule consisting of less than the complete coding sequence of a *S. avermitilis* aveR2 gene product or aveR2-related homologous polypeptide of the present invention, but comprising at least about 25%, and more preferably at least about 30%, of said nucleotide sequence, and that is useful in practicing the invention, as usefulness is defined above for aveR2-related polynucleotide molecules.

In a non-limiting embodiment, the substantial portion of the aveR2-related polynucleotide molecule consists of a nucleotide sequence that encodes a peptide fragment of a *S. avermitilis* aveR2 gene product or aveR2-related homologous polypeptide of the present invention. A "peptide fragment" of an aveR2-related polypeptide refers to a polypeptide consisting of a sub-sequence of the amino acid sequence of a full-length aveR2 gene product or homologous polypeptide, which sub-sequence is shorter in length than the full-length aveR2 gene product or homologous polypeptide, and which sub-sequence is useful in practicing the invention, as usefulness is defined above for aveR2-related polypeptides. In a preferred embodiment, the present invention provides a polynucleotide molecule consisting of a nucleotide sequence encoding a peptide fragment consisting of a sub-sequence of the amino acid sequence of SEQ ID NO:4. Peptide fragments of the invention are preferably at least about 15 amino acid residues in length.

The aveR2-related polynucleotide molecules disclosed herein can be used to express the aveR2 gene product, to prepare novel strains of Streptomyces in which the aveR2 gene has been mutated, and also to identify aveR2 homolog genes in other bacterial species or strains using known techniques. Thus, the present invention further provides an isolated polynucleotide molecule comprising a nucleotide sequence encoding an aveR2 homolog gene product. As used herein, an "aveR2 homolog gene product" is defined as a gene product encoded by an aveR2 homolog gene which, in turn, is defined in relation to the aveR2 gene as a gene from a different species of Streptomyces, or the closely related Saccharopolyspora genus and which is recognized by those of skill in the art as a homolog of the aveR2 gene of *S. avermitilis* based on a degree of nucleotide sequence identity greater than about 80%, and which also contains the conserved active site residues typically found in response regulator components of two-component signaling systems, and which is also closely linked to the regulated antibiotic biosynthetic genes. For example, aveR2 homology comparisons with eubacterial two-component systems from the Nar/Deg subgroup show 100% conservation of two aspartate residues (D), one of which is the site of phosphorylation, and a conserved lysine residue (K). As used herein, the term "aveR2 homolog gene includes the *S. avermitilis* aveR2 gene itself.

Methods for identifying polynucleotide clones containing aveR2 homolog genes are known in the art. For example, a polynucleotide molecule comprising a portion of the *S. avermitilis* aveR2 ORF can be detectably labeled and used to screen a genomic library constructed from DNA derived from the organism of interest. The stringency of the hybridization conditions can be selected based on the relationship of the reference organism, in this example *S. avermitilis*, to the organism of interest. Genomic DNA libraries can be screened for aveR2 homolog gene coding sequences using the techniques cited above in Section 5.1.1. Polynucleotide molecules having nucleotide sequences known to include the aveR2 ORF, as shown in SEQ ID NO:3, or oligonucleotide molecules representing portions thereof, can be used as probes in these screening experiments. Alternatively, oligonucleotide probes can be synthesized that correspond to nucleotide sequences deduced from the amino acid sequence of the purified aveR2 gene product.

Clones identified as containing aveR2 homolog gene coding sequences can be tested for appropriate biological function. For example, the clones can be subjected to sequence analysis in order to identify a suitable reading frame, as well as initiation and termination signals. The cloned DNA sequence can then be inserted into an appropriate expression vector which is then transformed into cells of a strain of *S. avermitilis* that have been rendered aveR2 to test for complementation. Transformed *S. avermitilis* host cells can then be analyzed for avermectin production using methods such as HPLC analysis of fermentation products, as described, e.g., in Section 6.6, below.

The present invention further provides an isolated polynucleotide molecule comprising one or more nucleotide sequences that naturally flank the aveR2 ORF of *S. avermitilis* in situ. Such flanking sequences can be selected from the nucleotide sequence of SEQ ID NO:3 from about nt 1 to about nt 2313, and from about nt 3022 to about nt 5045. The present invention further provides an isolated polynucleotide molecule comprising one or more nucleotide sequences that are homologous to nucleotide sequences that naturally flank the aveR2 ORF of *S. avermitilis* in situ. As used herein, a nucleotide sequence is homologous to a nucleotide sequence which naturally flanks the aveR2 ORF of *S. avermitilis* in situ where the homologous nucleotide sequence hybridizes to the complement of the nucleotide sequence which naturally flanks the aveR2 ORF of *S. avermitilis* in situ under moderately stringent conditions, i.e., hybridization to filter-bound DNA in 0.5 M $NaHPO_4$, 7% SDS, 1 mM EDTA at 65° C., and washing in 0.2×SSC/0.1% SDS at 42° C. (see Ausubel et al., 1989, above), and is useful in practicing the invention, as usefulness is defined above for aveR2-related polynucleotide molecules. Each flanking sequence, or homolog thereof, in the isolated polynucleotide molecule of the present invention is preferably at least about 200 nt in length. In a non-limiting embodiment, the present invention provides an isolated polynucleotide molecule comprising one or more of the aforementioned nucleotide sequences that naturally flank the aveR2 ORF of *S. avermitilis* in situ, or that are homologous to such nucleotide sequences, and further comprising one of the aforementioned aveR2-related nucleotide sequences of the present invention such as, e.g., the nucleotide sequence of the aveR2 ORF as shown in SEQ ID NO:3 from about nt 2314 to about nt 3021 or a substantial portion thereof.

5.1.3. aveR1/aveR2-Related Polynucleotide Molecules

The present invention further provides an isolated polynucleotide molecule comprising a nucleotide sequence encoding both the aveR1 and aveR2 gene products from *S. avermitilis* (referred to below as "aveR1/aveR2"). In a preferred embodiment, the aveR1 and aveR2 gene products comprise the amino acid sequences of SEQ ID NO:2 and SEQ ID NO:4, respectively. In a non-limiting embodiment, the isolated aveR1/aveR2 polynucleotide molecule comprises the nucleotide sequence of the aveR1 ORF of *S. avermitilis* as shown in SEQ ID NO:1 from about nt 1112 to about nt 2317, and the aveR2 ORF of *S. avermitilis* as shown in SEQ ID NO:1 from about nt 2314 to about nt 3021. In a further non-limiting embodiment, the isolated aveR1/aveR2 polynucleotide molecule comprises the nucleotide sequence of SEQ ID NO:1 from about nt 1112 to about nt 3021. In a further non-limiting embodiment, the isolated polynucleotide molecule comprises the nucleotide sequence of SEQ ID NO:1. The nucleotide sequence of SEQ ID NO:1 shows a partial overlap between the ORFs of aveR1 and aveR2; however, the present invention also includes aveR1/aveR2 polynucleotide molecules in which the ORFs for aveR1 and aveR2 do not overlap.

The present invention further provides an isolated polynucleotide molecule that is homologous to a polynucleotide molecule comprising a nucleotide sequence of the aveR1 ORF of *S. avermitilis* as shown in SEQ ID NO:1 from about nt 1112 to about nt 2317, and the aveR2 ORF of *S. avermitilis* as shown in SEQ ID NO:1 from about nt 2314 to about nt 3021. The term "homologous" when used in this respect means a polynucleotide molecule comprising a nucleotide sequence: (a) that encodes the same polypeptides as the aveR1 and aveR2 ORFs as shown in SEQ ID NO:1 from about nt 1112 to about nt 2317, and from about nt 2314 to about nt 3021, respectively, but that includes one or more silent changes to the nucleotide sequence according to the degeneracy of the genetic code; or (b) that hybridizes to the complement of a polynucleotide molecule comprising a nucleotide sequence that encodes a first polypeptide comprising the amino acid sequence of SEQ ID NO:2 and a second polypeptide comprising the amino acid sequence of SEQ ID NO:4, under moderately stringent conditions, i.e., hybridization to filter-bound DNA in 0.5 M $NaHPO_4$, 7% SDS, 1 mM EDTA at 65° C., and washing in 0.2×SSC/0.1% SDS at 42° C. (Ausubel et al., 1989, above), and is useful in practicing the invention. In a preferred embodiment, the homologous polynucleotide molecule hybridizes to the complement of a polynucleotide molecule comprising a nucleotide sequence that encodes a first polypeptide comprising the amino acid sequence of SEQ ID NO:2 and a second polypeptide comprising the amino acid sequence of SEQ ID NO:4, under highly stringent conditions, i.e., hybridization to filter-bound DNA in 0.5 M $NaHPO_4$, 7% SDS, 1 mM EDTA at 65° C., and washing in 0.1×SSC/0.1% SDS at 68° C. (Ausubel et al., 1989, above), and is useful in practicing the invention. In a further preferred embodiment, the homologous polynucleotide molecule hybridizes under highly stringent conditions to the complement of a polynucleotide molecule comprising the nucleotide sequence of the aveR1 and aveR2 ORFs of *S. avermitilis* as shown in SEQ ID NO:1 from about nt 1112 to about nt 2317, and from about nt 2314 to about nt 3021, respectively, and is useful in practicing the invention. In a further preferred embodiment, the homologous polynucleotide molecule has a nucleotide sequence having at least about 70%, more preferably at least about 80%, and most preferably at least about 90% sequence identity to the nucleotide sequence of the aveR1 and aveR2 ORFs of *S. avermitilis* as shown in SEQ ID NO:1 from about nt 1112 to about nt 2317, and from about nt 2314 to about nt 3021, respectively, as determined by any standard nucleotide sequence identity algorithm, such as BLASTN (GENBANK, NCBI), and hybridizes under highly stringent conditions to the complement of such a polynucleotide molecule, and is useful in practicing the invention.

As used herein, an aveR1/aveR2-related polynucleotide molecule is "useful in practicing the invention" where the polynucleotide molecule can be used to introduce mutations into either the aveR1 ORF or aveR2 ORF, or into both aveR1 and aveR2 ORFs, of *S. avermitilis*, by site-directed mutagenesis, such as by homologous recombination, or to amplify a polynucleotide molecule comprising the nucleotide sequence of either the aveR1 ORF or aveR2 ORF, or both the aveR1 and aveR2 ORFs, of *S. avermitilis* using standard amplification techniques. Such homologous polynucleotide molecules can include naturally occurring aveR1/ aveR2 genes present, in other species of Streptomyces or in other strains of *S. avermitilis*, as well as mutated aveR1 or aveR2 alleles, whether naturally occurring, chemically synthesized, or genetically engineered.

The present invention further provides an isolated polynucleotide molecule comprising a nucleotide sequence that encodes first and second polypeptides having amino acid sequences that are homologous to the amino acid sequences of SEQ ID NOS:2 and 4, respectively. As used herein to refer to polypeptides having amino acid sequences that are homologous to the amino acid sequences of the aveR1 and aveR2 gene products from *S. avermitilis*, the term "homologous" means polypeptides comprising the amino acid sequences of SEQ ID NOS:2 and 4, respectively, but in which one or more amino acid residues thereof has been conservatively substituted with a different amino acid residue, as conservative amino acid substitutions are defined above, where the resulting polypeptides are useful in practicing the invention. In a preferred embodiment, the homologous polypeptides have at least about 70%, more preferably at least about 80%, and most preferably at least about 90% amino acid sequence identity to the amino acid sequences of SEQ ID NO:2 and SEQ ID NO:4, respectively, as determined by any standard amino acid sequence identity algorithm, such as BLASTP (GENBANK, NCBI).

The present invention further provides an isolated polynucleotide molecule consisting of a nucleotide sequence that is a substantial portion of any of the aforementioned aveR1/aveR2-related polynucleotide molecules of the present invention. As used herein, a "substantial portion" of an aveR1 /aveR2-related polynucleotide molecule means a polynucleotide molecule consisting of less than the complete coding sequence required to encode both aveR1 and aveR2 gene products from *S. avermitilis*, or both aveR1 and aveR2-related homologous polypeptides of the present invention, but comprising at least about 10%, and more preferably at least about 20%, of said nucleotide sequence, and that is useful in practicing the invention, as usefulness is defined above for aveR1 laveR2-related polynucleotide molecules. In a preferred embodiment, the substantial portion of the aveR1aveR2-related polynucleotide molecule consists of a nucleotide sequence that encodes either the *S. avermitilis* aveR1 gene product or the *S. avermitilis* aveR2 gene product of the present invention, or homologous polypeptides thereof. In a specific though non-limiting embodiment, the substantial portion of the aveR1/aveR2-related polynucleotide molecule consists of the nucleotide sequence of the aveR1 ORF as shown in SEQ ID NO:1 from about nt1112 to about nt 2317. In another specific though non-limiting embodiment, the substantial portion of the aveR1/aveR2-related polynucleotide molecule consists of the nucleotide sequence of the aveR2 ORF as shown in SEQ ID NO:3 from about nt 2314 to about nt 3021.

The present invention further provides an isolated polynucleotide molecule comprising one or more nucleotide sequences that naturally flank the aveR1/aveR2 ORFs of *S. avermitilis* in situ. Such flanking sequences can be selected from the nucleotide sequence of SEQ ID NO:1 from about nt 1 to about nt 1111, and from about nt 3022 to about nt 5045. The present invention further provides an isolated polynucleotide molecule comprising one or more nucleotide sequences that are homologous to nucleotide sequences that naturally flank the aveR1/aveR2 ORFs of *S. avermitilis* in situ. As used herein, a nucleotide sequence is homologous to a nucleotide sequence which naturally flanks the aveR1/aveR2 ORFs of *S. avermitilis* in situ where the homologous nucleotide sequence hybridizes to the complement of the nucleotide sequence which naturally flanks the aveR1/aveR2 ORFs of *S. avermitilis* in situ under moderately stringent conditions, i.e., hybridization to filter-bound DNA in 0.5 M $NaHPO_4$, 7% SDS,1 mM EDTA at 65° C., and washing in 0.2×SSC 0.1% SDS at 42° C. (see Ausubel et al., 1989, above), and is useful in practicing the invention, as usefulness is defined above for an aveR1/aveR2-related polynucleotide molecule. Each flanking sequence, or homoblog thereof, in the isolated polynucleotide molecule of the present invention is preferably at least about 200 nt in length. In a non-limiting embodiment, the present invention provides an isolated polynucleotide molecule comprising one or more of the aforementioned nucleotide sequences that naturally flank the aveR1 /aveR2 ORFs of *S. avermitilis* in situ, or that are homologous to such nucleotide sequences, and further comprising one of the aforementioned aveR1/aveR2-related nucleotide sequences of the present invention such as, e.g., a nucleotide sequence encoding either or both of the aveR1 and aveR2 ORFs of *S. avermitilis* as shown in SEQ ID NO:1 from about nt 1112 to about nt 3021.

5.2. Oligonucleotide Molecules

The present invention further provides oligonucleotide molecules that hybridize to any of the aforementioned polynucleotide molecules of the present invention, or that hybridize to a polynucleotide molecule having a nucleotide sequence that is the complement of any of the aforementioned polynucleotide molecules of the present invention. Such oligonucleotide molecules are preferably at least about 10 nucleotides in length, but can extend up to the length of any sub-sequence of any of the aforementioned polynucleotide molecules of the present invention, and can hybridize to one or more of the aforementioned polynucleotide molecules under moderately or highly stringent conditions. For shorter oligonucleotide molecules, an example of highly stringent conditions includes washing in 6×SSC/0.5% sodium pyrophosphate at about 37° C. for ~14-base oligos, at about 48° C. for ~17-base oligos, at about 55° C. for ~20-base oligos, and at about 60° C. for ~23-base oligos. For longer oligonucleotide molecules (i.e., greater than about 100 nts), examples of moderately and highly stringent conditions are described in Section 5.1 above for homologous polynucleotide molecules. Hybridization conditions can be appropriately adjusted as known in the art, depending upon the particular oligonucleotide molecules utilized.

In a preferred embodiment, an oligonucleotide molecule of the present invention hybridizes under highly stringent conditions to a polynucleotide molecule consisting of the nucleotide sequence of SEQ ID NO:1, or to a polynucleotide molecule consisting of a nucleotide sequence that is the complement of the nucleotide sequence of SEQ ID NO:1.

The oligonucleotide molecules of the present invention are useful for a variety of purposes, including as primers in amplifying an aveR1 or aveR2 gene product-encoding polynucleotide molecule, or as anti-sense molecules useful in regulating ave genes and avermectin biosynthesis in Streptomyces. Amplification can be carried out using suitably designed oligonucleotide molecules in conjunction with standard techniques, such as the polymerase chain reaction (PCR), although other amplification techniques known in the art, e.g., the ligase chain reaction, can also be used. For example, for PCR, a mixture comprising suitably designed primers, a template comprising the nucleotide sequence to be amplified, and appropriate PCR enzymes and buffers, is prepared and processed according to standard protocols to amplify a specific aveR1- or aveR2-related polynucleotide sequence of the template.

5.3. Recombinant Expression Systems
5.3.1. Expression Vectors

The present invention further provides recombinant cloning vectors and recombinant expression vectors comprising a polynucleotide molecule of the present invention, which vectors are useful in cloning or expressing said polynucleotide molecules, including polynucleotide molecules comprising either the aveR1 ORF or the aveR2 ORF, or both the aveR1 and aveR2 ORFs, of S. avermitilis. In a non-limiting embodiment, the present invention provides plasmid pSE201 (ATCC 203182), which comprises the entire aveR1 ORF and the entire aveR2 ORF of S. avermitilis.

The following description is intended to apply to all of the aforementioned polynucleotide molecules and polypeptides of the present invention, including polynucleotide molecules comprising either or both of the aveR1 and aveR2 ORFs from S. avermitilis and their gene products, and all homologous polynucleotide molecules, homologous polypeptides, substantial portions of such polynucleotide molecules, and peptide fragments of such gene products and polypeptides, as defined above, unless otherwise indicated.

A variety of different vectors have been developed for specific use in Streptomyces, including phage, high copy number plasmids, low copy number plasmids, suicide plasmids, temperature-sensitive plasmids, and E coli-Streptomyces shuttle vectors, among others, and any of these can be used to practice the present invention. A number of drug resistance genes have also been cloned from Streptomyces, and several of these genes have been incorporated into vectors as selectable markers. Examples of current vectors for use in Streptomyces are presented, among other places, in Hutchinson, 1980, *Applied Biochem. Biotech.* 16:169–190.

Recombinant vectors of the present invention, particularly expression vectors, are preferably constructed so that the coding sequence for the polynucleotide molecule of the present invention is in operative association with one or more regulatory elements necessary for transcription and translation of the coding sequence to produce a polypeptide. As used herein, the term "regulatory element" includes but is not limited to nucleotide sequences that encode inducible and noninducible promoters, enhancers, operators and other elements known in the art that serve to drive and/or regulate expression of polynucleotide coding sequences. Also, as used herein, the coding sequence is in "operative association" with one or more regulatory elements where the regulatory elements effectively regulate and allow for the transcription of the coding sequence or the translation of its mRNA, or both.

Typical plasmid vectors that can be engineered to contain a polynucleotide molecule of the present invention include pCR-Blunt, pCR2.1 (Invitrogen), pGEM3Zf (Promega), and the shuttle vector pWHM3 (Vara etal., 1989, J. Bact. 171:5872–5881), among many others.

The regulatory elements of these vectors can vary in their strength and specificities. Depending on the hostvector system utilized, any of a number of suitable transcription and translation elements can be used. Non-limiting examples of transcriptional regulatory regions or promoters for bacteria include the β-gal promoter, the T7 promoter, the TAC promoter, λ left and right promoters, trp and lac promoters, trp-lac fusion promoters and, more specifically for Streptomyces, the promoters ermE, meIC., and tipA, etc.

Methods are well-known in the art for constructing recombinant vectors containing particular coding sequences in operative association with appropriate regulatory elements, and any of these can be used to practice the present invention. These methods include in vitro recombinant techniques, synthetic techniques, and in vivo genetic recombination. See, e.g., the techniques described in Maniatis et al., 1989, above: Ausubel et al, 1989, above; Sambrook et al., 1989, above; Innis et al., 1995, above; Erlich, 1992, above; and Hopwood et al., 1985, above.

Fusion protein expression vectors can be used to express an aveR1 or an aveR2 gene product-fusion protein. The purified fusion protein can be used to raise antisera against the aveR1 or aveR2 gene product, to study the biochemical properties of the aveR1 or aveR2 gene product, to engineer aveR1 or aveR2 fusion proteins with different biochemical activities, or to aid in the identification or purification of the expressed aveR1 or aveR2 gene product in recombinant expression systems. Possible fusion protein expression vectors include but are not limited to vectors incorporating sequences that encode β-galactosidase and trpE fusions, maltose binding protein fusions, glutathione-S-transferase fusions and polyhistidine fusions (carrier regions).

AveR1 or AveR2 fusion proteins can be engineered to comprise a region useful for purification. For example, AveR1- or AveR2-maltose-binding protein fusions can be purified using amylose resin; AveR1- or AveR2-glutathione-S-transferase fusion proteins can be purified using glutathione-agarose beads; and AveR1- or AveR2-polyhistidine fusions can be purified using divalent nickel resin. Alternatively, antibodies against a carrier protein or peptide can be used for affinity chromatography purification of the fusion protein. For example, a nucleotide sequence coding for the target epitope of a monoclonal antibody can be engineered into the expression vector in operative association with the regulatory elements and situated so that the expressed epitope is fused to the AveR1 or AveR2 polypeptide. For example, a nucleotide sequence coding for the FLAG™ epitope tag (International Biotechnologies Inc.), which is a hydrophilic marker peptide, can be inserted by standard techniques into the expression vector at a point corresponding to the amino or carboxyl terminus of the AveR1 or AveR2 polypeptide. The expressed AveR1 or AveR2 polypeptide-FLAG™ epitope fusion product can then be detected and affinity-purified using commercially available anti- FLAG™0 antibodies.

The expression vector encoding the AveR1 or AveR2 fusion protein can also be engineered to contain polylinker sequences that encode specific protease cleavage sites so that the expressed AveR1 or AveR2 polypeptide can be released from the carrier region or fusion partner by treatment with a specific protease. For example, the fusion protein vector can include DNA sequences encoding thrombin or factor Xa cleavage sites, among others.

A signal sequence upstream from and in reading frame with the aveR1 or aveR2 ORF can be engineered into the expression vector by known methods to direct the trafficking and secretion of the expressed gene product. Non-limiting examples of signal sequences include those from α-factor, immunoglobulins, outer membrane proteins, penicillinase, and T-cell receptors, among others.

To aid in the selection of host cells transformed or transfected with cloning or expression vectors of the present invention, the vector can be engineered to further comprise a coding sequence for a reporter gene product or other selectable marker. Such a coding sequence is preferably in operative association with the regulatory element coding sequences, as described above. Reporter genes which can be useful in the invention are well-known in the art and include those encoding green fluorescent protein, luciferase, xylE, and tyrosinase, among others. Nucleotide sequences encoding selectable markers are well-known in the art, and include those that encode gene products conferring resistance to antibiotics or anti-metabolites, or that supply an auxotrophic requirement. Examples of such sequences include those that encode resistance to erythromycin, thiostrepton or kanamycin, among many others.

5.3.2. Host Cells

The present invention further provides transformed host cells comprising a polynucleotide molecule or recombinant vector of the invention, and novel strains or cell lines derived therefrom. Host cells useful in the practice of the invention are preferably Streptomyces cells, although other prokaryotic cells or eukaryotic cells can also be used. Such transformed host cells typically include but are not limited to microorganisms, such as bacteria transformed with recombinant bacteriophage DNA, plasmid DNA or cosmid DNA vectors, or yeast transformed with recombinant vectors, among others.

Bacterial cells are generally preferred as host cells. It should be understood that the polynucleotide molecules of the present invention are intended to function in Streptomyces cells, but can also be transformed into other bacterial or eukaryotic cells, e.g., for cloning or expression purposes. A strain of *E. coli* can typically be used, such as, e.g., the DH5α strain, which is available either from the American Type Culture Collection (ATCC), Rockville, Md., USA (Accession No. 31343) or from commercial sources (Stratagene). Preferred eukaryotic host cells include yeast cells, although mammalian cells or insect cells can also be utilized effectively.

The recombinant expression vector of the invention is preferably transformed or transfected into one or more host cells of a substantially homogeneous culture of cells. The expression vector is generally introduced into host cells in accordance with known techniques, such as, e.g., by protoplast transformation, calcium phosphate precipitation, calcium chloride treatment, microinjection, electroporation, transfection by contact with a recombined virus, liposome-mediated transfection, DEAE-dextran transfection, transduction, conjugation, or microprojectile bombardment. Selection of transformants can be conducted by standard procedures, such as selecting for cells expressing a selectable marker, e.g., antibiotic resistance, associated with the recombinant vector, as described above.

Once the expression vector is introduced into the host cell, the integration and maintenance of the aveR1-, aveR2- or aveR1/aveR2-related coding sequence, either in the host cell chromosome or episomally, can be confirmed by standard techniques, e.g., by Southern hybridization analysis, restriction enzyme analysis, PCR analysis, including reverse transcriptase PCR (rt-PCR), or by immunological assay to detect the expected gene product. Host cells containing and/or expressing the recombinant aveR1-, aveR2- or aveR1/aveR2-related coding sequence can be identified by any of at least four general approaches which are well-known in the art, including: (i) DNA-DNA, DNA-RNA, or RNA-antisense RNA hybridization; (ii) detecting the presence of "marker" gene functions; (iii) assessing the level of transcription as measured by the expression of aveR1- or aveR2-specific mRNA transcripts in the host cell; and (iv) detecting the presence of mature polypeptide product as measured, e.g., by immunoassay or by the presence of AveR1 or AveR2 biological activity.

5.3.3. Expression and Characterization of A Recombinant aveR1 or aveR2 Gene Product Once the aveR1-, aveR2- or aveR1/aveR2-related coding sequence has been stably introduced into an appropriate host cell, the transformed host cell is clonally propagated, and the resulting cells are grown under conditions conducive to the maximum production of the aveR1- and/or aveR2-related gene products. Such conditions typically include growing cells to high density. Where the expression vector comprises an inducible promoter, appropriate induction conditions such as, e.g., temperature shift, exhaustion of nutrients, addition of gratuitous inducers (e.g., analogs of carbohydrates, such as isopropyl-β-D-thiogalactopyranoside (IPTG)), accumulation of excess metabolic by-products, or the like, are employed as needed to induce expression.

Where the expressed aveR1- and/or aveR2-related gene product is retained inside the host cells, the cells are harvested and lysed, and the product is isolated and purified from the lysate under extraction conditions known in the art to minimize protein degradation such as, e.g., at 4° C., or in the presence of protease inhibitors, or both. Where the expressed aveR1 and/or aveR2 gene product is secreted from the host cells, the exhausted nutrient medium can simply be collected and the product isolated therefrom.

The expressed aveR1- and/or aveR2-related gene product can be isolated or substantially purified from cell lysates or culture medium, as appropriate, using standard methods, including but not limited to any combination of the following methods: ammonium sulfate precipitation, size fractionation, ion exchange chromatography, HPLC, density centrifugation, and affinity chromatography. Where the expressed aveR1- and/or aveR2-related gene products exhibit biological activity, increasing purity of the preparation can be monitored at each step of the purification procedure by use of an appropriate assay. Whether or not the expressed aveR1- and/or aveR2-related gene products exhibit biological activity, each can be detected as based, e.g., on size, or reactivity with an antibody otherwise specific for AveR1 or AveR2, or by the presence of a fusion tag.

The present invention thus provides a substantially purified or isolated polypeptide encoded by a polynucleotide molecule of the present invention. In a specific though non-limiting embodiment, the polypeptide is an aveR1 gene product from *S. avermitilis* comprising the amino acid sequence of SEQ ID NO:2. In another specific though non-limiting embodiment, the polypeptide is an aveR2 gene product from *S. avermitilis* comprising the amino acid sequence of SEQ ID NO:4. The present invention further provides substantially purified or isolated polypeptides that are homologous to either the aveR1 or aveR2 gene products of the present invention. The present invention further provides peptide fragments of the aveR1 or aveR2 gene products or homologous polypeptides of the present invention. The substantially purified or isolated polypeptides of the present invention are useful for a variety of purposes, such as, e.g., screening for compounds that alter aveR1 or aveR2 gene product function, thereby modulating avermectin biosynthesis, and for raising antibodies directed against aveR1 or aveR2 gene products.

As used herein, a polypeptide is "substantially purified" where the polypeptide constitutes the majority by weight of the material in a particular preparation. Also, as used herein, a polypeptide is "isolated" where the polypeptide constitutes at least about 90 wt% of the material in a particular preparation.

The present invention further provides a method of preparing a substantially purified or isolated aveR1 gene product, aveR2 gene product, homologous polypeptide, or peptide fragment of the present invention, comprising culturing a host cell transformed or transfected with a recombinant expression vector, said recombinant expression vector comprising a polynucleotide molecule comprising a nucleotide sequence encoding the aveR1 gene product, aveR2 gene product, homologous polypeptide, or peptide fragment, respectively, wherein the nucleotide sequence is in operative association with one or more regulatory elements, under conditions conducive to the expression of the particular gene product, polypeptide, or peptide fragment, and recovering the expressed gene product, polypeptide, or peptide fragment, from the cell culture in a substantially purified or isolated form.

Once an aveR1 or aveR2 gene product of sufficient purity has been obtained, it can be characterized by standard methods, including by SDS-PAGE, size exclusion chromatography, amino acid sequence analysis, biological activity in producing appropriate products in the avermectin biosynthetic pathway, etc. For example, the amino acid sequence of the aveR1 or aveR2 gene product can be determined using standard peptide sequencing techniques. The aveR1 or aveR2 gene product can be further characterized using hydrophilicity analysis (see, e.g., Hopp and Woods, 1981, Proc. Natl. Acad. Sci. USA 78:3824), or analogous software algorithms, to identify hydrophobic and hydrophilic regions of the aveR1 or aveR2 gene product. Structural analysis can be carried out to identify regions of the aveR1 or aveR2 gene product that assume specific secondary structures. Biophysical methods such as X-ray crystallography (Engstrom, 1974, *Biochem. Exp. Biol.* 11:7–13), computer modeling (Fletterick and Zoller (eds), 1986, in: *Current Communications in Molecular Biology*, Cold Spring Harbor Laboratory, Cold Spring Harbor, N.Y.), and nuclear magnetic resonance (NMR) can be used to map and study sites of interaction between the aveR1 or aveR2 gene products and their substrates. Information obtained from these studies can be used to select new sites for mutation in the aveR1 or aveR2 ORFs to help develop new strains of Streptomyces having more desirable avermectin production characteristics.

5.4. Construction of aveR1 and aveR2 Mutants

The present invention further provides compositions and methods for genetically modifying the cells of a species or strain of Streptomyces, including genetic constructs such as gene replacement vectors. In a preferred embodiment, the cells of a species or strain of Streptomyces are genetically modified to produce an amount of avermectins which is detectably different from the amount of avermectins produced by cells of the same species or strain that have not been so modified. In a more preferred embodiment, the cells of a strain of *S. avermitilis* are genetically modified to produce a detectably increased amount of avermectins compared to the amount of avermectins produced by cells of the same strain that have not been so modified. According to the present invention, such genetic modification preferably comprises mutating either the aveR1 homolog gene, or the aveR2 homolog gene, or both the aveR1 and aveR2 homolog genes, where such mutation results in a detectable increase in the amount of avermectins produced by cells of a strain of Streptomyces carrying the gene mutation compared to cells of the same strain that do not carry the gene mutation. In a preferred embodiment, such genetic modification preferably comprises mutating either the aveR1 gene, or the aveR2 gene, or both the aveR1 and aveR2 genes, of *S. avermitilis*, where such mutation results in a detectable increase in the amount of avermectins produced by cells of a strain of *S. avermitilis* carrying the gene mutation compared to cells of the same strain that do not carry the gene mutation.

According to the present invention, mutations can be introduced into either the aveR1 homolog gene or the aveR2 homolog gene, or into both aveR1 and aveR2 homolog genes, using any techniques presently known or to be developed in the future. For example, random mutagenesis can be carried out using standard mutagenic techniques, including exposing Streptomyces cells to ultraviolet radiation or x-rays, or to chemical mutagens such as N-methyl-N'-nitrosoguanidine, ethyl methane sulfonate, nitrous acid or nitrogen mustards, and then selecting for cells exhibiting detectably increased avermectin production as the result of one or more mutations in the aveR1 and/or aveR2 homolog genes. See, e.g., Ausubel, 1989, above, for a review of mutagenesis techniques.

Alternatively, mutations to the aveR1 or aveR2 homolog genes, or to both the aveR1 and aveR2 homolog genes, can be carried out in a site-directed manner using any of a variety of known recombinant methods, including error-prone PCR, or cassette mutagenesis. For example, site-directed mutagenesis that takes advantage of homologous recombination can be utilized to specifically alter the ORF of either the aveR1 or aveR2 homolog gene or flanking sequence thereof, or the ORF of both the aveR1 and aveR2 homolog genes or flanking sequences thereof, so as to specifically introduce one or more mutations into these genes. In addition, the methods described in U.S. Pat. No. 5,605,793, comprising random fragmentation, repeated cycles of mutagenesis, and nucleotide shuffling, can be used to generate large libraries of polynucleotide molecules having nucleotide sequences encoding aveR1 and/or aveR2 homolog gene mutations.

Mutations to the aveR1 or aveR2 homolog genes, or to both the aveR1 and aveR2 homolog genes, that are useful in practicing the invention include addition, deletion or substitution, or some combination thereof, of one or more nucleotides in either the aveR1 gene or aveR2 homolog genes, or in both the aveR1 and aveR2 homolog genes, or in flanking regulatory regions, and which produce the desired result, i.e., a detectable increase in the amount of avermectins produced by cells of a strain of Streptomyces carrying the gene mutation compared to cells of the same species or strain of Streptomyces which do not carry the gene mutation. Such mutations can serve to introduce one or more novel restriction sites, termination codons, or frame shifts, into either or both of the ORF sequences or into the flanking regulatory regions involved in gene transcription. Other useful mutations include those which insert a different or heterologous nucleotide sequence into either or both of the aveR1 and aveR2 homolog genes; or which delete all or a portion of either or both of the aveR1 and aveR2 homolog genes,; or which replace all or a portion of either or both of the aveR1 and aveR2 homolog genes with a different or heterologous nucleotide sequence; and which mutations produce the desired result, i.e., a detectable increase in the amount of avermectins produced by cells of a species or strain of Streptomyces carrying the gene mutation compared to cells of the same species or strain of Streptomyces which do not carry the gene mutation. In a preferred embodiment, the mutation serves to inactive the aveR1 or aveR2 homolog gene, or both the aveR1 and aveR2 homolog genes. In a more preferred embodiment, the mutation serves to inactivate either the aveR2 homolog gene, or both the aveR1 and aveR2 homolog genes.

Site-directed mutations are useful, particularly where they serve to alter one or more conserved amino acid residues in either the aveR1 or aveR2 homolog gene product, or in both the aveR1 and aveR2 homolog gene products. For example, a comparison of the deduced amino acid sequences of aveR1 and aveR2 gene products from *S. avermitilis* with analogous gene products from *S. coelicolor*, as presented in FIGS. 1A and 1B, indicates sites of significant conservation of amino acid residues between these species. Site-directed mutagenesis which deletes or non-conservatively substitutes one or more of these conserved amino acid residues can be particularly effective in producing novel mutant strains that exhibit desirable alterations in avermectin production.

In a preferred embodiment, one or more mutations are introduced by homologous recombination into either the aveR1 or aveR2 homolog gene, or into both the aveR1 and aveR2 homolog genes, using a genetic construct provided by the present invention, such as, e.g., a gene replacement vector. The genetic construct can comprise the entire ORF of the aveR1 homolog gene or a homologous polynucleotide molecule thereof, or a substantial portion thereof; or the entire ORF of the aveR2 homolog gene or a homologous polynucleotide molecule thereof, or a substantial portion thereof; or the entire ORFs of both the aveR1 and aveR2 homolog genes or a homologous polynucleotide molecule thereof, or a substantial portion thereof; or nucleotide sequences that naturally flank the ORF of either the aveR1 homolog gene or aveR2 homolog gene, or both the aveR1 and aveR2 homolog genes in situ; or a combination thereof; and which genetic construct can be used to introduce a mutation into either the aveR1 homolog gene or the aveR2 homolog gene, or into both the aveR1 and aveR2 homolog genes, which mutation results in a detectable increase in the amount of avermectins produced by cells of a species or strain of Streptomyces carrying said gene mutation compared to cells of the same species or strain which do not carry the gene mutation.

In a specific though non-limiting embodiment, a genetic construct for use in practicing the present invention is a plasmid which comprises a polynucleotide molecule comprising a nucleotide sequence that is otherwise the same as the nucleotide sequence of the ORF of either the aveR1 or aveR2 homolog gene, or both the aveR1 and aveR2 homolog genes, or a substantial portion thereof, from Streptomyces, but which further comprises one or more mutations, i.e., one or more nucleotide deletions, insertions, substitutions, or a combination thereof, which plasmid can be used to transform cells of Streptomyces, and thereby introduce the mutation into the aveR1 homolog gene, aveR2 homolog gene, or into both the aveR1 and aveR2 homolog genes, so as to disrupt or otherwise alter the activity or biological function of either the aveR1 homolog gene, or aveR2 homolog gene, or both the aveR1 and aveR2 homolog genes, respectively, or to disrupt or otherwise alter the activity or biological function of the aveR1 homolog gene product, or aveR2homolog gene product, or both aveR1 and aveR2 homolog gene products, respectively, such that the amount of avermectins produced by cells of a species or strain of Streptomyces carrying said gene mutation will be detectably increased compared to cells of the same species or strain which do not carry the gene mutation. Such a plasmid preferably further comprises a selectable marker.

Once transformed into host cells of Streptomyces, the polynucleotide molecule of the genetic construct is specifically targeted by homologous recombination to the aveR1 homolog gene or aveR2 homolog gene, or to both the aveR1 and aveR2 homolog genes, and either replaces the aveR1 homolog gene or a portion thereof, or the aveR2 homolog gene or a portion thereof, or both the aveR1 and aveR2 homolog genes or a portion thereof, or inserts into the aveR1 homolog gene or aveR2 homolog gene. As a result of this recombination event, either the aveR1 homolog gene or the aveR2 homolog gene, or both the aveR1 and aveR2 homolog genes, of the host cell, or the gene products encoded thereby, are partially or completely disabled. Transformed cells are selected, preferably by taking advantage of the presence of a selectable marker in the genetic construct, and screened by standard techniques, such as those described in Section 6.6 below, for those cells that produce a detectably increased amount of avermectins compared to cells of the same strain which have not be so transformed.

In a specific though non-limiting embodiment exemplified in Section 6.9.1 below, a gene replacement vector was used to disrupt both the aveR1 and aveR2 genes of *S. avermitilis* by replacing a portion of the ORF of each gene with a heterologous nucleotide sequence (ermE). In another specific though non-limiting embodiment exemplified in Section 6.9.2 below, a gene replacement vector was used to disrupt the aveR2 gene of *S. avermitilis* by inserting a heterologous nucleotide sequence (ermE) into the aveR2 ORF. Each of these gene replacement vectors were separately transformed into cells of a strain of *S. avermitilis* and integrated into the chromosome by homologous recombination. Fermentation analysis of each of these novel *S. avermitilis* transformants indicated a significant increase in the amount of avermectins produced by cells carrying these gene mutations compared to cells of the same strain that do not carry either of these gene mutations.

The present invention further provides a method for identifying a mutation of an aveR1 homolog gene or aveR2 homolog gene, or of both aveR1 and aveR2 homolog genes, in a species or strain of Streptomyces, which gene mutation is capable of detectably increasing the amount of avermectins produced by cells of the species or strain of Streptomyces carrying the gene mutation compared to cells of the same species or strain of Streptomyces that do not carry the gene mutation, comprising: (a) measuring the amount of avermectins produced by cells of a particular species or strain of Streptomyces; (b) introducing a mutation into the aveR1 homolog gene or aveR2 homolog gene, or into both the aveR1 and aveR2 homolog genes, of cells of the species or strain of Streptomyces of step (a); and (c) comparing the amount of avermectins produced by the cells carrying the gene mutation as produced in step (b) to the amount of avermectins produced by the cells of step (a) that do not carry the gene mutation; such that if the amount of avermectins produced by the cells carrying the gene mutation as produced in step (b) is detectably higher than the amount of avermectins produced by the cells of step (a) that do not carry the gene mutation, then a mutation of the aveR1 or aveR2 homolog gene, or of both the aveR1 and aveR2 homolog genes, capable of detectably increasing the amount of avermectins produced has been identified. In a preferred embodiment, the species of Streptomyces is *S. avermitilis*.

The present invention further provides a method of preparing genetically modified cells from a species or strain of Streptomyces, which modified cells produce a detectably increased amount of avermectins compared to unmodified cells of the same species or strain, comprising mutating the aveR1 homolog gene or the aveR2 homolog gene, or both the aveR1 and aveR2 homolog genes of Streptomyces, in cells of the species or strain of Streptomyces, and selecting the mutated cells which produce a detectably increased amount of avermectins compared to cells of the same species or strain of Streptomyces that do not carry the gene mutation. In a preferred embodiment, the species of Streptomyces is *S. avermitilis*.

The present invention further provides novel strains of Streptomyces, the cells of which produce a detectably increased amount of avermectins as a result of one or more mutations to the aveR1 homolog gene or aveR2 homolog gene, or to both the aveR1 and aveR2 homolog genes, compared to cells of the same species or strain of Streptomyces that do not carry the gene mutation. In a preferred embodiment, the species of Streptomyces is S. avermitilis. The novel strains of the present invention are useful in the large-scale production of avermectins, such as the commercially desirable doramectin.

The present invention further provides a process for producing an increased amount of avermectins produced by cultures of Streptomyces, comprising culturing cells of a species or strain of Streptomyces, which cells comprise a mutation in the aveR1 homolog gene or aveR2 homolog gene, or in both the aveR1 and aveR2 homolog genes, which gene mutation serves to detectably increase the amount of avermectins produced by cells of the species or strain of Streptomyces carrying the gene mutation compared to cells of the same species or strain that do not carry the gene mutation, in culture media under conditions which permit or induce the production of avermectins therefrom, and recovering the avermectins from the culture. In a preferred embodiment, the species of Streptomyces is S. avermitilis. This process is useful to increase the production efficiency of avermectins.

5.5. Anti-Sense Oligonucleotides and Ribozymes

Also within the scope of the present invention are oligonucleotide sequences that include anti-sense oligonucleotides, phosphorothioates and ribozymes that function to bind to, degrade and/or inhibit the translation of aveR1 or aveR2 homolog gene mRNA.

Anti-sense oligonucleotides, including anti-sense RNA molecules and anti-sense DNA molecules, act to directly block the translation of mRNA by binding to targeted mRNA and preventing protein translation. For example, antisense oligonucleotides of at least about 15 bases and complementary to unique regions of the DNA sequence encoding an AveR1 or AveR2 homolog polypeptide can be synthesized, e.g., by conventional phosphodiester techniques.

Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hammerhead motif ribozyme molecules that specifically and efficiently catalyze endonucleolytic cleavage of aveR1 or aveR2 homolog mRNA sequences are also within the scope of the present invention.

Specific ribozyme cleavage sites within any potential RNA target are initially identified by scanning the target molecule for ribozyme cleavage sites which include the following sequences, GUA, GUU, and GUC. Once identified, short RNA sequences of between about 15 and 20 ribonucleotides corresponding to the region of the target gene containing the cleavage site can be evaluated for predicted structural features such as secondary structure that may render the oligonucleotide sequence unsuitable. The suitability of candidate targets can also be evaluated by testing their accessibility to hybridization with complementary oligonucleotides, using, e.g., ribonuclease protection assays.

Both the anti-sense oligonucleotides and ribozymes of the present invention can be prepared by known methods. These include techniques for chemical synthesis such as, e.g., by solid phase phosphoamite chemical synthesis. Alternatively, anti-sense RNA molecules can be generated by in vitro or in vivo transcription of DNA sequences encoding the RNA molecule. Such DNA sequences can be incorporated into a wide variety of vectors which incorporate suitable RNA polymerase promoters such as the T7 or SP6 polymerase promoters.

Various modifications to the oligonucleotides of the present invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

5.6. Antibodies

The present invention further provides polyclonal and monoclonal antibodies that bind to an aveR1 homolog gene product, aveR2 homolog gene product, or to an homologous polypeptide, or peptide fragment of the present invention. Such antibodies can be used as affinity reagents with which to purify a native aveR1 or aveR2 homolog gene product, or to analyze the activity or biological function of the aveR1 or aveR2 homolog gene products.

Antibodies can be raised against any of the aveR1- or aveR2-related polypeptides of the present invention. Various host animals, including but not limited to cows, horses, rabbits, goats, sheep, and mice, can be used according to known methods to produce anti-AveR1 or anti-AveR2-specific antibodies. Various adjuvants known in the art can be used to enhance antibody production.

Polyclonal antibodies can be obtained from immunized animals and tested for anti-AveR1 or anti-AveR2 specificity using standard techniques. Alternatively, monoclonal antibodies to an AveR1 or AveR2 polypeptide can be prepared using any technique that provides for the production of antibody molecules by continuous cell lines in culture. These include but are not limited to the hybridoma technique originally described by Kohler and Milstein (*Nature*, 1975, 256: 495–497); the human B-cell hybridoma technique (Kosbor, et al., 1983, Immunology Today 4:72; Cote, et al., 1983, *Proc. Natl. Acad. Sci. USA* 80: 2026–2030); and the EBV-hybridoma technique (Cole, et aL, 1985, *Monoclonal Antibodies and Cancer Therapy*, Alan R. Liss, Inc., pp. 77–96). Alternatively, techniques described for the production of single chain antibodies (see, e.g., U.S. Pat. No. 4,946,778) can be adapted to produce AveR1- or AveR2-specific single chain antibodies. These publications are incorporated herein by reference.

Antibody fragments that contain specific binding sites for an AveR1 or AveR2 polypeptide are also encompassed within the present invention, and can be generated by known techniques. Such fragments include but are not limited to $F(ab')_2$ fragments which can be generated by pepsin digestion of an intact antibody molecule, and Fab fragments which can be generated by reducing the disulfide bridges of the $F(ab')_2$ fragments. Alternatively, Fab expression libraries can be constructed (Huse et al., 1989, Science 246: 1275–1281) to allow rapid identification of Fab fragments having the desired specificity to the AveR1 or AveR2 polypeptide.

Techniques for the production of monoclonal antibodies and antibody fragments are well-known in the art, and are additionally described, among other places, in Harlow and Lane, 1988, *Antibodies: A Laboratory Manual*, Cold Spring Harbor Laboratory; and in J. W. Goding, 1986, *Monoclonal*

*Antibodies: Principles and Practice*, Academic Press, London. All of the above-cited publications are incorporated herein by reference.

5.7. Uses of Avermectins

Avermectins are highly active antiparasitic agents having particular utility as anthelmintics, ectoparasiticides, insecticides and acaricides, and avermectins prepared using the compositions and methods of the present invention are useful for any of these purposes.

The avermectins prepared according to the present invention are useful to treat various diseases or conditions in humans, particularly where those diseases or conditions are caused by parasitic infections, as known in the art. See, e.g., Ikeda and Omura, 1997, Chem. Rev. 97(7):2591–2609.

The avermectins prepared according to the present invention are effective in treating a variety of conditions caused by endoparasites including, e.g., helminthiasis, which is most frequently caused by a group of parasitic nematodes, and which can cause disease in humans, and severe economic losses in swine, sheep, poultry, horses and cattle, as well as affecting the health of domestic animals. Thus, avermectins prepared according to the present invention are effective against nematodes that affect humans, as well as those that affect various species of animals including, e.g., Dirofilaria in dogs, and various parasites which infect humans, including gastrointestinal parasites such as Ancylostoma, Necator, Ascaris, Strongyloides, Trinchinella, Capillaria, Trichuris, Enterobius, and parasites which are found in the blood or other tissues or organs, such as filarial worms and the extract intestinal states of Strongyloides and Trichinella.

The avermectins prepared according to the present invention are also useful in treating ectoparasitic infections including, e.g., arthropod infestations of mammals and birds, caused by ticks, mites, lice, fleas, blowflies, biting insects, or migrating dipterous larvae which can affect cattle and horses, among others.

The avermectins prepared according to the present invention are also useful as insecticides against household pests such as, e.g., the cockroach, clothes moth, carpet beetle and the housefly among others, as well as insect pests of stored grain and of agricultural plants, which pests include spider mites, aphids, caterpillars, and orthopterans such as locusts, among others.

Animals that can be treated with the avermectins of the present invention include sheep, cattle, horses, deer, goats, swine, birds including poultry, and dogs and cats.

The avermectins prepared according to the present invention are administered in a formulation appropriate to the specific intended use, the particular species of host animal being treated, and the parasite or insect involved. For use as a parasiticide, an avermectin of the present invention can be administered orally in the form of a capsule, bolus, tablet or liquid drench or, alternatively, can be administered as a pour-on, or by injection, or as an implant. Such formulations are prepared in a conventional manner in accordance with standard veterinary practice. Thus, capsules, boluses or tablets can be prepared by mixing the active ingredient with a suitable finely divided diluent or carrier additionally containing a disintegrating agent and/or binder such as starch, lactose, talc, magnesium stearate, etc. A drench formulation can be prepared by dispersing the active ingredient in an aqueous solution together with a dispersing or wetting agent, etc. Injectable formulations can be prepared in the form of a sterile solution which can contain other substances such as, e.g., sufficient salts and/or glucose to make the solution isotonic with blood.

Such formulations will vary with regard to the weight of active compound depending on the patient, or on the species of host animal to be treated, the severity and type of infection, and the body weight of the host. Generally, for oral administration a dose,of active compound of from about 0.001 to 10 mg per kg of patient or animal body weight given as a single dose or in divided doses for a period of from 1 to 5 days will be satisfactory. However, there can be instances where higher or lower dosage ranges are indicated, as determined, e.g., by a physician or veterinarian, as based on clinical symptoms.

As an alternative, an avermectin prepared according to the present invention can be administered in combination with animal feedstuff, and for this purpose a concentrated feed additive or premix can be prepared for mixing with the normal animal feed.

For use as an insecticide, and for treating agricultural pests, the compounds of the present invention can be applied as sprays, dusts, emulsions and the like in accordance with standard agricultural practice.

The following examples are illustrative only, and are not intended to limit the scope of the present invention.

6. EXAMPLE: ISOLATION OF aveR1 AND aveR2 GENES

This example describes the isolation and characterization of two novel *S. avermitilis* genes that encode aveR1 and aveR2 gene products and that are involved in the regulation of avermectin biosynthesis.

6.1. Growth of *S. avermitilis* for DNA Isolation

Single colonies of *S. avermitilis* ATCC 31272 (single colony isolate #2) were isolated on 1/2 strength YPD-6 medium containing: Difco Yeast Extract—5 g; Difco Bacto-peptone—5 g; Dextrose—2.5 g; MOPS—5 g; Difco Bacto agar—15 g. Final volume was adjusted to 1 liter with $dH_2O$, pH was adjusted to 7.0, and the medium was autoclaved at 121° C. for 25 min. The mycelia grown in the above medium were used to inoculate 10 ml of TSB medium (Difco Tryptic Soy Broth in 1 liter $dH_2O$, autoclaved at 121° C. for 25 min) in a 25 mm×150 mm tube which was maintained with shaking (300 rpm) at 28° C. for 48–72 hrs.

6.2. Chromosomal DNA Isolation From *S. avermitilis*

Aliquots (0.25 ml or 0.5 ml) of mycelia grown as described above were placed in 1.5 ml microcentrifuge tubes and the cells were concentrated by centrifugation at 12,000 ×g for 60 sec. The supernatant was discarded and the cells were resuspended in 0.25 ml TSE buffer (20 ml 1.5 M sucrose, 2.5 ml 1 M Tris HCI, pH 8.0, 2.5 ml 1 M EDTA, pH 8.0, and 75 ml $dH_2O$) containing 2 mg/ml lysozyme. The samples were incubated at 37° C. for 20 min with shaking, loaded into an AutoGen 540™ automated nucleic acid isolation instrument (Integrated Separation Systems, Natick, Mass.) and genomic DNA was isolated using Cycle 159 (equipment software) according to manufacturer's instructions.

Alternatively, 5 ml of mycelia were placed in a 17 mm×100 mm tube, the cells were concentrated by centrifugation at 3,000 rpm for 5 min, and the supernatant was removed. Cells were resuspended in 1 ml TSE buffer, concentrated by centrifugation at 3,000 rpm for 5 min and the supernatant was removed. Cells were resuspended in 1 ml TSE buffer containing 2 mg/ml lysozyme and incubated at 37° C. with shaking for 30–60 min. After incubation, 0.5 ml 10% SDS was added and the cells incubated at 37° C. until lysis was complete. The lysate was incubated at 65° C. for 10 min, cooled to rm temp, split into two 1.5 ml Eppendorf tubes and extracted 1× with 0.5 ml phenol/chloroform (50% phenol previously equilibrated with 0.5 M Tris, pH 8.0; 50% chloroform). The aqueous phase was removed and extracted 2–5× with chloroform:isoamyl alcohol (24:1). The DNA was precipitated by adding 1/10 volume 3M sodium acetate, pH 4.8, incubating the mixture on ice for 10 min, centrifuging the mixture at 15,000 rpm at 5° C. for 10 min, and removing the supernatant to a clean tube to which 1 volume of isopropanol was added. The mixture was then incubated on ice for 20 min, centrifuged at 15,000 rpm for 20 min at 5° C., the supernatant was removed, and the DNA pellet was washed 1× with 70% ethanol. After the pellet was dry, the DNA was resuspended in TE buffer (10 mM Tris, 1 mM EDTA, pH 8.0).

6.3. Plasmid DNA Isolation From *S. avermitilis*

An aliquot (1.0 ml) of mycelia was placed in 1.5 ml microcentrifuge tubes and the cells were concentrated by centrifugation at 12,000×g for 60 sec. The supernatant was discarded, the cells were resuspended in 1.0 ml 10.3% sucrose and concentrated by centrifugation at 12,000×g for 60 sec, and the supernatant was discarded. The cells were then resuspended in 0.25 ml TSE buffer containing 2 mg/ml lysozyme, incubated at 37° C. for 20 min with shaking, and loaded into the AutoGen 540™ automated nucleic acid isolation instrument. Plasmid DNA was isolated using Cycle 106 (equipment software) according to manufacturer's instructions.

Alternatively, 1.5 ml of mycelia were placed in 1.5 ml microcentrifuge tubes and the cells were concentrated by centrifugation at 12,000×g for 60 sec. The supernatant was discarded, the cells were resuspended in 1.0 ml 10.3% sucrose and concentrated by centrifugation at 12,000×g for 60 sec, and the supernatant was discarded. The cells were resuspended in 0.5 ml TSE buffer containing 2 mg/ml lysozyme and incubated at 37° C. for 15–30 min. After incubation, 0.25 ml alkaline SDS (0.3N NaOH, 2% SDS) was added and the cells incubated at 55° C. for 15–30 min or until the solution was clear. Sodium acetate (0.1 ml, 3M, pH 4.8) was then added to the DNA solution, which was incubated on ice for 10 min. The DNA samples were centrifuged at 14,000 rpm for 10 min at 5° C. The supernatant was removed to a clean tube, and 0.2 ml phenol:chloroform (50% phenol:50% chloroform) was added and gently mixed. The DNA solution was centrifuged at 14,000 rpm for 10 min at 5° C. and the upper layer was removed to a clean Eppendorf tube. Isopropanol (0.75 ml) was added, and the solution was gently mixed and then incubated at rm temp for 20 min. The DNA solution was centrifuged at 14,000 rpm for 15 min at 5° C., the supernatant was removed, the DNA pellet was washed with 70% ethanol, dried, and the DNA was resuspended in TE buffer.

6.4. Plasmid DNA Isolation From *E. coli*

A single transformed *E. coli* colony was inoculated into 5 ml Luria-Bertani (LB) medium (Bacto-Tryptone—10 g; Bacto-yeast extract—5 g; and NaCl—10 g in 1 liter dH$_2$O, pH 7.0, autoclaved at 121° C. for 25 min) supplemented with 100 µg/ml ampicillin. The culture was incubated overnight, and a 1 ml aliquot placed in a 1.5 ml microcentrifuge tube. The culture samples were loaded into the AutoGen 540™ automated nucleic acid isolation instrument and plasmid DNA was isolated using Cycle 3 (equipment software) according to manufacturers instructions.

6.5. Preparation And Transformation of *S. avermitilis* Protoplasts

Single colonies of *S. avermitilis* were isolated on 1/2 strength YPD—6. The mycelia were used to inoculate 10 ml of TSB medium in a 25 mm×150 mm tube which was then incubated with shaking (300 rpm) at 28° C. for 48 hrs. One ml of mycelia was used to inoculate 50 ml YEME medium. YEME medium contains per liter: Difco Yeast Extract—3 g; Difco Bacto-peptone—5 g; Difco Malt Extract—3 g; and sucrose—300 g. After autoclaving at 121° C. for 25 min, the following were added: 2.5 M MgCl$_2$. 6H$_2$O (separately autoclaved at 121° C. for 25 min)—2 ml; and glycine (20%) (filter-sterilized)—25 ml.

The mycelia were grown at 30° C. for 48–72 hrs and harvested by centrifugation in a 50 ml centrifuge (Falcon) tube at 3,000 rpm for 20 min. The supernatant was discarded and the mycelia were resuspended in P buffer which contains: sucrose—205 g; K$_2$SO$_4$—0.25 g; MgCl$_2$ 6H$_2$O—2.02 g; H$_2$O—600 ml; K$_2$PO$_4$(0.5%)—10 ml; Trace element solution*—20 mg; CaCl$_2$H$_2$O(3.68%)—100 ml; MES buffer (1.0 M, pH 6.5)—10 ml. (*Trace element solution contains per liter: ZnCl$_2$—40 mg; FeCl$_3$.6H$_2$O—200 mg; CuCl$_2$.2H$_2$O—10 mg; Na$_2$B$_4$O$_7$. 10H$_2$O—10 mg; (NH$_4$)$_6$Mo$_7$O$_{24}$. 4H$_2$O—10 mg). The pH was adjusted to 6.5, final volume was adjusted to 1 liter, and the medium was filtered hot through a 0.45 micron filter.

The mycelia were pelleted at 3,000 rpm for 20 min, the supernatant was discarded, and the mycelia was resuspended in 20 ml P buffer containing 2 mg/ml lysozyme. The mycelia were incubated at 35° C. for 15 min with shaking, and checked microscopically to determine extent of protoplast formation. When protoplast formation was complete, the protoplasts were centrifuged at 8,000 rpm for 10 min. The supernatant was removed and the protoplasts were resuspended in 10 ml P buffer. The protoplasts were centrifuged at 8,000 rpm for 10 min, the supernatant was removed, the protoplasts were resuspended in 2 ml P buffer, and approximately 1 × 10$^9$ protoplasts were distributed to 2.0 ml cryogenic vials (Nalgene).

A vial containing 1×10$^9$ protoplasts was centrifuged for 10 min at 8,000 rpm, the supernatant was removed, and the protoplasts were resuspended in 0.1 ml P buffer. Two to 5 tg of transforming DNA were added to the protoplasts, immediately followed by the addition of 0.5 ml working T buffer. T buffer base contains: PEG 1000 (Sigma)—25 g; sucrose—2.5 g; and H$_2$O—83 ml. The pH was adjusted to 8.8 with 1 N NaOH (filter-sterilized), and the T buffer base was filter-sterilized and stored at 4° C. Working T buffer, made the same day used, contains T buffer base—8.3 ml; K$_2$PO$_4$(4 mM)—1.0 ml; CaCl$_2$. 2H$_2$O(5 M)—0.2 ml; and TES (1 M, pH 8)—0.5 ml. Each component of the working T buffer was filter-sterilized and stored at 4° C.

Within 20 sec of adding T buffer to the protoplasts, 1.0 ml P buffer was also added and the protoplasts were centrifuged at 8,000 rpm for 10 min. The supernatant was discarded and the protoplasts were resuspended in 0.1 ml P buffer. The protoplasts were then plated on RM14 media which contains: sucrose—205 g; K$_2$SO$_4$—0.25 g; MgCl$_2$.6H$_2$O—10.12 g; glucose—10 g; Difco Casamino Acids—0.1 g; Difco Yeast Extract—5 g; Difco Oatmeal Agar—3 g; Difco Bacto Agar—22 g; and H$_2$O—800 ml. The solution was autoclaved at 121° C. for 25 min. After autoclaving, sterile stocks of the following were added: K$_2$PO$_4$(0.5%)—10 ml;

CaCl$_2$.2H$_2$O(5 M)—5 ml; L-proline (20%)—15 ml; MES buffer (1.0 M, pH 6.5)—10 ml; Trace element solution (same as above)—2 ml; cycloheximide stock (25 mg/ml)—40 ml; and 1N NaOH—2 ml. Twenty-five ml of RM14 medium were aliquoted per plate, and plates were dried for 24 hrs before use.

The protoplasts were incubated in 95% humidity at 30° C. for 20–24 hrs. To select erythromycin-resistant transformants, 1 ml of overlay buffer plus 125 μg erythromycin (to give a final concentration of 5 pg/ml erythromycin) was spread evenly over the RM14 regeneration plates. Overlay buffer contains per 100 ml: sucrose—10.3 9; Trace element solution (same as above)—0.2 ml; and MES (1 M, pH 6.5)—1 ml. The protoplasts were incubated in 95% humidity at 30° C. for 7–14 days until erythromycin-resistant (Erm$^r$) colonies were visible.

6.6. Fermentation Analysis of S. avermitilis Strains

S. avermitilis mycelia grown on 1/2 strength YPD-6 for 4–7 days were inoculated into 1×6 inch tubes containing 8 ml of preform medium and two 5 mm glass beads. Preform medium contains: soluble starch (either thin boiled starch or KOSO, Japan Com Starch Co., Nagoya)—20 g/L; Pharmamedia (Traders Protein, Memphis Tenn.)—15 g/L; Ardamine pH (Champlain, Inc. Clifton, N.J.)—5 g/L; CaCO$_3$—2 g/L; 2× bcfa ("bcfa" refers to branched chain fatty acids) containing a final concentration in the medium of 50 ppm 2-(±)-methyl butyric acid, 60 ppm isobutyric acid, and 20 ppm isovaleric acid. The pH was adjusted to 7.2, and the medium was autoclaved at 121° C. for 25 min.

The tube was shaken at a 17° angle at 215 rpm at 29° C. for 3 days. A 2-ml aliquot of the seed culture was used to inoculate a 300 ml Erlenmeyer flask containing 25 ml of production medium which contains: starch (either thin boiled starch or KOSO)—160 g/L; Nutrisoy (Archer Daniels Midland, Decatur, Ill.)—10 g/L; Ardamine pH—10 g/L; K$_2$HPO$_4$—2 g/L; MgSO$_4$.4H$_2$O—2 g/L; FeSO$_4$.7H$_2$O—0.02 g/L; MnCl$_2$—0.002 g/L; ZnSO$_4$.7H$_2$O—0.002 g/L; CaCO$_3$—14 g/L; and 2× bcfa (as above). The pH was adjusted to 6.9 and the medium was autoclaved at 121° C. for 25 min.

After inoculation, the flask was incubated at 29° C. for 12 days with shaking at 200 rpm. After incubation, a 2 ml sample was withdrawn from the flask, diluted with 8 ml of methanol, mixed, and the mixture was centrifuged at 1250×g for 10 min to pellet debris. The supernatant was then assayed by high performance liquid chromatography (HPLC) using a Beckman Ultrasphere ODS column (25 cm×4.6 mm ID) with a flow rate of 0.75 mvmin and detection by absorbance measurements at 240 nm. The mobile phase was 86/8.9/5.1 methanol/water/acetonitrile.

6.7. Identification and Isolation of S. avermitilis PKS Genes

A cosmid library of S. avermitilis (ATCC 31272) chromosomal DNA was prepared and hybridized with a ketosynthase (KS) probe made from a fragment of the Saccharopolyspora erythraea polyketide synthase (PKS) gene. A detailed description of the preparation of cosmid libraries can be found in Sambrook et al., 1989, above. A detailed description of the preparation of Streptomyces chromosomal DNA libraries is presented in Hopwood et al., 1985, above. Cosmid clones containing ketosynthase-hybridizing regions were identified by hybridization to a 2.7 Kb NdeI/Eco47III fragment from pEX26 (kindly supplied by Dr. P. Leadley, Cambridge, UK). Approximately 5 μg of pEX26 were digested using the restriction endonucleases NdeI and Eco47III. The reaction mixture was loaded on a 0.8% SeaPlaque™ GTG agarose gel (FMC BioProducts, Rockland, Me.). The 2.7 Kb NedI/Eco47III fragment was excised from the gel after electrophoresis and the DNA was recovered from the gel using GELase™ (Epicentre Technologies) using the Fast Protocol. The 2.7 Kb NedI/Eco47III fragment was labeled with [α-$^{32}$P]dCTP (deoxycytidine 5'-triphosphate, tetra (triethylammonium) salt, [α-$^{32}$P]-) (NEN-Dupont, Boston, Mass.) using the BRL Nick Translation System (BRL Life Technologies, Inc., Gaithersburg, Md.), following the supplier's instructions. A typical reaction was performed in 0.05 ml volume. After addition of 5 μl Stop buffer, the labeled DNA was separated from unincorporated nucleotides using a G-25 Sephadex Quick Spin™ Column (Boehringer Mannheim) following the supplier's instructions.

Approximately 1800 cosmid clones were screened by colony hybridization. Ten clones were identified that hybridized strongly to the Sacc. erythraea KS probe. E. coli colonies containing cosmid DNA were grown in LB liquid medium and cosmid DNA was isolated from each culture in the AutoGen 540™ automated nucleic acid isolation instrument using Cycle 3 (equipment software) according to manufacturer's instructions. Restriction endonuclease mapping and Southern blot hybridization analyses revealed that five of the clones contained overlapping chromosomal regions. An S. avermitilis genomic BamHI restriction map of the five cosmids (i.e., pSE65, pSE66, pSE67, pSE68, pSE69) was constructed by analysis of overlapping cosmids and hybridizations (FIG. 4).

6.8. Identification of Regulatory Gene ORFs

Figure 2B:
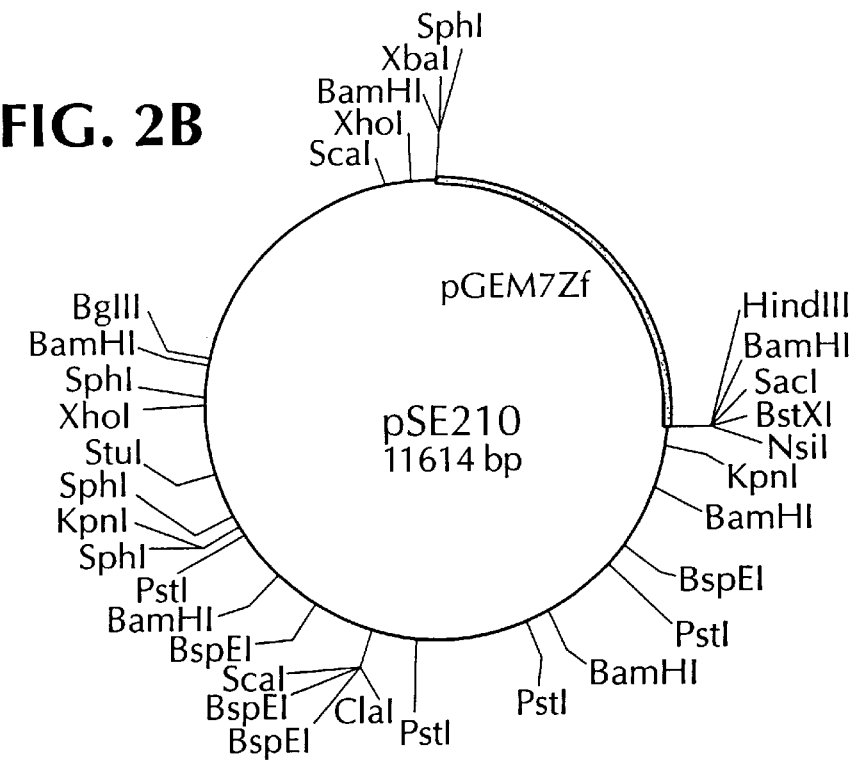

The following methods were used to subclone fragments derived from the pSE68 clone. pSE68 (5 μg) was digested with XbaI and EcoRI. The reaction mixture was loaded on a 0.8% SeaPlaque™ GTG agarose gel (FMC BioProducts), a ~19 Kb XbaI/EcoRI fragment was excised from the gel after electrophoresis, and the DNA was recovered from the gel using GELase™ (Epicentre Technologies) using the Fast Protocol. Approximately 5 μg of pGEM7Zf(+) (Promega) was digested with XbaI and EcoRI. About 0.5 μg of the 19 Kb EcoRI/Xba1 fragment and 0.5 μg of digested pGEM7Zf (+) were mixed together and incubated overnight with 1 unit of ligase (New England Biolabs, Inc., Beverly, Mass.) at 15° C. in a total volume of 20 μl according to supplier's instructions. After incubation, 5 μl of the ligation mixture was incubated at 70° C. for 10 min, cooled to rm temp, and used to transform competent E. coli DH5α cells (BRL) according to manufacturer's instructions. Plasmid DNA was isolated from ampicillin-resistant transformants and the presence of the ~19 Kb XbaI/EcoRI insert was confirmed by restriction analysis. This plasmid was designated as pSE200.

pSE200 was further modified by Exonuclease III digestion using the Erase-a-Base System (Promega) following manufacturer's instructions. Five μg of pSE200 were digested with ClaI. ClaI generates 5' protrusions which were protected from exonuclease digestion by being filled in with alpha-phosphorothioate deoxyribonucleotides according to manufacturer's instructions. pSE200 was then digested with EcoRI and aliquots were digested with S1 nuclease for varying times ranging from 30 seconds to 12 min. S1 nuclease-treated samples of pSE200 were ligated overnight and transformed into E. coli HB101 (BRL) competent cells following manufacturer's instructions. Plasmid DNA was isolated from ampicillin-resistant transformants and the size of the insert DNA was determined by restriction enzyme analysis. One isolate was identified that contained a ~5.9 Kb insert, and this isolate was designated as pSE201 (FIG. 2A) and deposited with the ATCC (Accession No. 203182). A second isolate was identified that contained a ~8.8 Kb insert, and this isolate was designated as pSE210 (FIG. 2B).

Approximately 10 µg of pSE201 were isolated using a plasmid DNA isolation kit (Qiagen, Valencia, Calif.) following manufacturer's instructions. This DNA was sequenced using an ABI 373A Automated DNA Sequencer (Perkin Elmer, Foster City, Calif.). Sequence data was assembled and edited using Genetic Computer Group programs (GCG, Madison, Wis.). The DNA sequence of the ORFs of the regulatory genes, aveR1 and aveR2, are presented identically in both SEQ ID NO:1 and SEQ ID NO:3. The aveR1 ORF is from nt 1112 to nt 2317 of SEQ ID NO:1. The aveR2 ORF is from nt 2314 to nt 3021 of SEQ ID NO:1.

A comparison of the amino acid sequence deduced from the aveR1 ORF of S. avermitilis (SEQ ID NO:2) shows 32% identity to the deduced absA1 gene product of S coelicolor (SEQ ID NO:5) (FIG. 1A) (Brian et al., 1996, J. Bacteriology 178:3221–3231). A comparison of the amino acid sequence deduced from the aveR2 ORF of S. avermitilis (SEQ ID NO:4) shows 45% identity to the deduced absA2 gene product of S coelicolor (SEQ ID NO:6) (FIG. 1B).

6.9. Construction and Use of Gene Replacement Vectors

A general description of techniques for introducing mutations into Streptomyces genes is provided by Kieser and Hopwood, 1991, Meth. Enzym. 204:430–458. A more detailed description is provided by Anzai et al. 1998, J. Antibiot. XLI(2):226–233; Stutzman-Engwall et al., 1992, J. Bacteriol. 174(1):144–154; and Oh and Chater, 1997, J. Bact. 179:122–127. These publications are incorporated herein by reference.

6.9.1. Inactivation of Both aveR1 and aveR2 Genes

Both the aveR1 and aveR2 genes were inactivated by replacing a 988 bp Bg/II/StuI fragment in pSE210 (FIG. 2B) with the erythromycin resistance gene (ermE) from Saccharopolyspora erythraea, as follows. Approximately 5 µg of pSE210 was digested with Bg/II and StuI to release a ~10.8 Kb fragment. The Bg/II end was filled in by incubating the DNA with 100 µM final concentration of dNTPs in 1× Klenow buffer and 1 U Klenow enzyme (Boehringer Mannheim) for 30 min at 37° C. The ~10.8 Kb fragment was purified from an agarose gel and incubated in 1× alkaline phosphatase buffer and 1U alkaline phosphatase for 1 hr at 50° C. to dephosphorylate the ends. After incubation, the dephosphorylated fragment was purified by phenol/chloroform extraction as described in Section 6.3 and resuspended in TE buffer. The ermE gene was isolated from pIJ4026 (provided by the John Innes Institute, Norwich, U. K.; see also Bibb et al., 1985, Gene 41:357–368) by digestion with Bg/II, and the Bg/II ends were filled in by incubating the ermE fragment with 100 µM final concentration of dNTPs in 1× Klenow buffer and 1 U Klenow enzyme for 30 min at 37° C. The ~1.7 Kb ermE fragment was purified from an agarose gel and 0.5 µg mixed with 0.5 µg of the ~10.8 Kb fragment and ligated. The ligation mixture was used to transform competent E. coli HB101 cells (BRL) following manufacturers instructions. Plasmid DNA was isolated from ampicillin-resistant transformants and the presence of the ermE insert was confirmed by restriction analysis. This plasmid, which was designated as pSE214 (FIG. 3A), was transformed into E. coli DM1 (BRL), and plasmid DNA was isolated from ampicillin-resistant transformants. The insertion of the ermE gene in place of the 988 bp Bg/II/StuI fragment removes 752 bp from the aveR1 gene and 232 bp from the aveR2 gene.

pSE214, which will not replicate autonomously in S. avermitilis, was used as a gene replacement vector for integrative gene replacement as follows. Eight µl of pSE214 DNA (1 µg) was denatured by adding 2 µl of 1 M NaOH, incubating for 10 min at 37° C., then rapidly chilling on ice, followed by adding 2 µl of 1 M HCl, according to the procedure of Oh and Chater, 1997, above. S. avermitilis protoplasts were transformed with the denatured pSE214. Transformants were regenerated under selective conditions requiring expression of the erythromycin gene so as to induce integrative gene recombination of the plasmid into the host cell chromosome. Since the plasmid does not replicate autonomously, erythromycin-resistant-transformants should have the plasmid sequences integrated into the chromosome by either a single homologous recombination event between one of the two DNA segments that flank the ermE gene and its homologous counterpart in the chromosome, which will result in the integration of the entire pSE214 vector, or a double cross-over where a second recombination event occurs between the second DNA segment that flanks the mutation and its homologous counterpart in the chromosome, which will result in the exchange of aveR1/aveR2 (inactivated) sequences from the plasmid into the chromosome and the concomitant loss of the wild-type allele and the vector sequences from the chromosome. Erythromycin-resistant transformants were isolated and screened by PCR for the presence of the vector backbone. All transformants were missing the vector backbone, suggesting that a double cross-over event had taken place and the chromosomal aveR1/aveR2 sequences had been replaced by the aveR1/aveR2 deleted sequences. Erythromycin-resistant transformants were analyzed by HPLC analysis of fermentation products. S. avermitilis strains containing an aveR1/aveR2 deletion produced an average of 3.4 times as much total avermectins as the control strain (TABLE 1).

6.9.2. Inactivation of the aveR2 Gene

The aveR2 gene was inactivated by inserting the ermE gene into a Bg/II site in pSE210 (FIG. 2B), and using the resulting plasmid as a gene replacement vector in S. avermitilis, as follows. Approximately 5 µg of pSE210 were digested with Bg/II. The linearized pSE210 was then incubated in 1× alkaline phosphatase buffer and 1U alkaline phosphatase to dephosphorylate the ends for 1 hr at 50° C. The ermE gene was isolated from pIJ4026 by digestion with Bg/II, followed by electrophoresis, and the ~1.7 Kb ermE gene was purified from the gel. About 0.5 µg of linearized pSE210 and 0.5 µg of the ermE fragment were mixed together and ligated. The ligation mixture was transformed into competent E. coli HB101 (BRL) following manufacturers instructions. Plasmid DNA was isolated from ampicillin-resistant transformants and the presence of the ermE insert was confirmed by restriction analysis. This plasmid, which was designated as pSE216 (FIG. 3B), was transformed into E. coli DM1 (BRL) following manufacturer's instructions, and plasmid DNA was isolated from ampicillin-resistant transformants.

pSE216, which will not replicate autonomously in S. avermitilis, was used as a gene replacement vector for integrative gene replacement as follows. Eight µl of pSE216 DNA (1 µg) was denatured by adding 2 µl 1M NaOH, incubating for 10 min at 37° C., then rapidly chilling on ice, followed by adding 2 µl of 1M HCl (Oh and Chater, 1997, above). S. avermitilis protoplasts were then transformed with denatured pSE216. Transformants were generated under selective conditions that require expression of the erythromycin gene to induce integrative gene recombination of the plasmid into the host cell chromosome. Since the plasmid does not replicate autonomously, erythromycin-resistant transformants should have the plasmid sequences integrated into the chromosome by either a single homologous recombination event between one of the two DNA segments that flank the ermE gene and its homologous counterpart in the chromosome, which will result in the integration of the entire pSE216 vector, or a double cross-over where a second recombination event occurs between the second DNA segment that flanks the mutation and its homologous counterpart in the chromosome, which will result in the exchange of the aveR2 (inactivated) sequences from the plasmid into the chromosome and the concomitant loss of the wild-type allele and the vector sequences from the chromosome. Erythromycin-resistant transformants were isolated and screened by PCR for the presence of the vector backbone. All transformants were missing the vector backbone, suggesting that a double cross-over event had taken place and the chromosomal aveR2 sequences had been replaced by the inactivated aveR2 sequence. Erythromycin-resistant transformants were analyzed by HPLC analysis of fermentation products. *S. avermitilis* strains containing an inactivated aveR2 gene produced an average of 3.1 times as much total avermectins as the control strain (TABLE 1).

TABLE 1

|  | Control (avg. of 5 cultures) | aveR1/aveR2 Deletion (avg. of 4 cultures) | aveR2 Insertion (avg. of 6 cultures) |
|---|---|---|---|
| Total Relative Amt. Of Avermectins | 1 | 3.4 | 3.1 |

DEPOSIT OF BIOLOGICAL MATERIALS

The following biological material was deposited with the American Type Culture Collection (ATCC) at 12301 Parklawn Drive, Rockville, Md., 20852, USA, on Sep. 9, 1998, and was assigned the following accession numbers:

| Plasmid | Accession No. |
|---|---|
| plasmid pSE201 | 203182 |

All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method of preparing genetically modified cells from a strain of *Streptomyces avermitilis*, which modified cells produce a detectably increased amount of avermectins compared to unmodified cells of the strain of *Streptomyces avermitilis*, comprising mutating the aveR1 gene or the aveR2 gene, or both the aveR1 and aveR2 genes, in cells of the strain of *Streptomyces avermitilis*, and selecting mutated cells which produce a detectably increased amount of avermectins compared to cells of the same strain of *Streptomyces avermitilis* that do not carry the gene mutation.

2. The method of claim 1, wherein the mutation is carried out by deleting a portion or all of the aveR1 gene or aveR2 gene, or by replacing a portion or all of the aveR1 gene or aveR2 gene with a different or heterologous nucleotide sequence.

3. The method of claim 1, wherein the mutation is carried out by deleting a portion or all of both the aveR1 and aveR2 genes, or by replacing a portion or all of both the aveR1 and aveR2 genes with a different or heterologous nucleotide sequence.

4. The method of claim 1, wherein the mutation is carried out by inserting a different or heterologous nucleotide sequence into either the aveR1 gene or aveR2 gene, or both the aveR1 gene and aveR2 gene.

* * * * *

SEQUENCE LISTING

```
<160> NUMBER OF SEQ ID NOS: 6

<210> SEQ ID NO 1
<211> LENGTH: 5045
<212> TYPE: DNA
<213> ORGANISM: Streptomyces avermitilis
<220> FEATURE:
<221> NAME/KEY: CDS
<222> LOCATION: (1112)..(2317)
<223> OTHER INFORMATION: aveR1 ORF

<400> SEQUENCE: 1
cgagttgctg gtcatcggcg tactcctccc ggcgactccg cccggtactc gaccgcggca      60
gcggtcagcc gcatgaacgc ctcttcgaga gacacggtct tccgcgtcac ctcgtgcacc     120
gtcacggcgt gcgccgcgac gagttcgccg atccgctccg cggcggcggc caccttcagg     180
ctgccgtcgg agcagtcggt gaccgtgatt cccgcgccga ccagcacgtc gcgcagccgc     240
cgcggttccg gagtgcgcac ccgcacccc acgtccgtgt acctgtcgat gaactcgctc      300
atgctggtgt ccgcgaggag ccgaccgcgg ccgatgatga cgaggtggtc cacggtgagc     360
gccgcctcgc tcatcagatg gctggacacg aagacggtgc gtccctgtgc cgccaggtcc     420
cgcatgaggt gccgcagcca caggacgcct tccgggtcga gcccgttgac cggctcgtcg     480
agcaccagga cggcggggtc gccgagcagc gccgcggcga ttcccagccg ctgactcatg     540
cccagcgaga acgtccccgc ccgccggcgc acggcgctcc gcaggcccgc cagctcgatc     600
acctcacgga cgcggcgggg cgggatccgg ttgctgcggg ccagccagcg caagtggttc     660
agcgcggttc ggccggggtg caccgccctg gcgtcgagca gtgcccccac cgtccgcagc     720
```

-continued

```
gggtcgcgga gccgctggta gggcgcgccg tcgatgcgta cctcgccggc cgtcgggcgg   780
tccaggccca gcatcatgcg catcgcggtg gacttcccgg cgccgttggg gccaaggaat   840
ccggtcaccc gaccggtccg tacctggaag gtaagaccct ccacaacggt ggtggtcccg   900
tagcgcttgg tcaggtccgt gacttcgatc atgccggtga tggtccgtga cgacaggctc   960
ccgccgcgtc ccgctcgggg ctgactgccc cttctccacc cccggttgga gaatgaccgc  1020
cacccgcggc cgcgcatcag gctgcaggag gagcggcttt gaccaccgct ggacggaggc  1080
```

```
ggagcggcgt acgcctggat atggtcgagc g gtg cat gca ggt acc gcg gtg   1132
                                    Val His Ala Gly Thr Ala Val
                                     1               5
```

| | | | | | | | | | | | | | | | | |
|---|---|---|---|---|---|---|---|---|---|---|---|---|---|---|---|---|
| gac | ccc | gac | gac | cat | ccg | atc | ctg | gcc | cgg | cga | ctg | agc | cgg | cgc | cga | 1180 |
| Asp | Pro | Asp | Asp | His | Pro | Ile | Leu | Ala | Arg | Arg | Leu | Ser | Arg | Arg | Arg | |
| | | 10 | | | | 15 | | | | 20 | | | | | | |

```
ctc atc gcc ctg gac ggc gtg ctc gta ttc gcc tac gca tgc gcg ctg   1228
Leu Ile Ala Leu Asp Gly Val Leu Val Phe Ala Tyr Ala Cys Ala Leu
        25               30                35 ctg tcg acc ggg ccg aca ggc atc tcg tcg tcg tcc gcg ccg ccg ctc   1276
Leu Ser Thr Gly Pro Thr Gly Ile Ser Ser Ser Ser Ala Pro Pro Leu
40              45                   50                     55 ccg gcc ccg gtg ccg tgg gag cgg ctc gtg ctc atc gcc gcg gcc act   1324
Pro Ala Pro Val Pro Trp Glu Arg Leu Val Leu Ile Ala Ala Ala Thr
                60                   65                  70 gcg cct gtc gcc gta cgg cgg atc tgg ccg ttg ccc gtg ttc gcg gtc   1372
Ala Pro Val Ala Val Arg Arg Ile Trp Pro Leu Pro Val Phe Ala Val
            75                  80                 85 gtg ctg gcg gtg acc gcc gtg gcc gtc gtg cgg gac gcg gcg tgg gac   1420
Val Leu Ala Val Thr Ala Val Ala Val Val Arg Asp Ala Ala Trp Asp
        90                  95                 100 ccg ttc ctg tcg gcg gcg ttc gcc ctc tac acc gtc gcc gtc acg gtg   1468
Pro Phe Leu Ser Ala Ala Phe Ala Leu Tyr Thr Val Ala Val Thr Val
    105                 110                115 ccc tcg cgc cac tgg tgg caa cgc tgg tta ccc ggc ctg gcg atc gct   1516
Pro Ser Arg His Trp Trp Gln Arg Trp Leu Pro Gly Leu Ala Ile Ala
120                 125                 130                  135 ttg ctg acc gtg gcc ggc ctt gcc gga gca gcg cgt gcc ggc gag gcc   1564
Leu Leu Thr Val Ala Gly Leu Ala Gly Ala Ala Arg Ala Gly Glu Ala
                140                 145                 150 ttc tgg tgg cgc ggc agc ccc ggt ctg ctg ctc ggc ttc gcc gca       1612
Phe Trp Trp Arg Gly Ser Pro Gly Leu Leu Leu Gly Phe Ala Ala
            155                 160                 165 ctg ctc ggc gcc tgg caa ctg gga cgc gcc gcg cgg cag agg cgc gca   1660
Leu Leu Gly Ala Trp Gln Leu Gly Arg Ala Ala Arg Gln Arg Arg Ala
        170                 175                 180 ttc gcc gtc cgg gcg gcc gag cag ctc gca caa cgg gcc gtc acg gag   1708
Phe Ala Val Arg Ala Ala Glu Gln Leu Ala Gln Arg Ala Val Thr Glu
    185                 190                 195 gaa cgc ctg cgg ata gcc cgc gaa ctg cat gac gtc gtc acg cac agc   1756
Glu Arg Leu Arg Ile Ala Arg Glu Leu His Asp Val Val Thr His Ser
200                 205                 210                 215 atg ggc ctg atc gcg gtc aag gtc ggc gtc gcc aac cac gtg ttg cac   1804
Met Gly Leu Ile Ala Val Lys Val Gly Val Ala Asn His Val Leu His
                220                 225                 230 atc agg ccg cag gag gcg tac gac gcg ctc cag gtc atc gaa cgc acg   1852
Ile Arg Pro Gln Glu Ala Tyr Asp Ala Leu Gln Val Ile Glu Arg Thr
        235                 240                 245 agc cgc acc gcg ctg aac gac atg cgc cgg atg ctc ggt gtg ctg cgt   1900
Ser Arg Thr Ala Leu Asn Asp Met Arg Arg Met Leu Gly Val Leu Arg
```

-continued

|  |  |  |  |  |  |  |  |  |  |  |  |  |  |  |  |
|---|---|---|---|---|---|---|---|---|---|---|---|---|---|---|---|
| | | 250 | | | | 255 | | | | | 260 | | | | |
| acg | tcc | gag | ggt | gag | cgg | cag | tca | gcg | gct | ctc | ggc | ccg | ctg | cct | ggc | 1948 |
| Thr | Ser | Glu | Gly | Glu | Arg | Gln | Ser | Ala | Ala | Leu | Gly | Pro | Leu | Pro | Gly |
| | | 265 | | | | 270 | | | | 275 | | | | |
| gcc | ctt | gct | ctc | cct | gac | ctc | gtc | ggg | cag | gcc | ggc | gcg | cag | ctg | act | 1996 |
| Ala | Leu | Ala | Leu | Pro | Asp | Leu | Val | Gly | Gln | Ala | Gly | Ala | Gln | Leu | Thr |
| 280 | | | | 285 | | | | 290 | | | | | 295 |
| atg | cgc | ggt | gtc | gag | agt | ctg | ccc | gac | gga | gtc | gcg | ctg | gcc | gtc | tac | 2044 |
| Met | Arg | Gly | Val | Glu | Ser | Leu | Pro | Asp | Gly | Val | Ala | Leu | Ala | Val | Tyr |
| | | | 300 | | | | 305 | | | | 310 | | | |
| cgg | atc | gtg | cag | gag | gcg | ctc | acc | aat | gtc | gcc | aag | cac | gcc | ggc | ccg | 2092 |
| Arg | Ile | Val | Gln | Glu | Ala | Leu | Thr | Asn | Val | Ala | Lys | His | Ala | Gly | Pro |
| | | 315 | | | | 320 | | | | 325 | | | | |
| gag | gcc | cgc | tgc | cgg | gtg | gcg | gtc | gat | gcg | aac | ggc | cac | ggc | gtc | cgg | 2140 |
| Glu | Ala | Arg | Cys | Arg | Val | Ala | Val | Asp | Ala | Asn | Gly | His | Gly | Val | Arg |
| | | 330 | | | | 335 | | | | | 340 | | | |
| ctc | gag | ata | acc | gac | gac | gga | ggc | gac | cgg | agc | ccc | ctc | gcg | ccg | aag | 2188 |
| Leu | Glu | Ile | Thr | Asp | Asp | Gly | Gly | Asp | Arg | Ser | Pro | Leu | Ala | Pro | Lys |
| 345 | | | | 350 | | | | 355 | | | | |
| ccc | ggc | ggc | cac | gga | atc | gtc | ggc | atg | cgc | gaa | cgc | gtc | gcc | ctg | tac | 2236 |
| Pro | Gly | Gly | His | Gly | Ile | Val | Gly | Met | Arg | Glu | Arg | Val | Ala | Leu | Tyr |
| 360 | | | | 365 | | | | | 370 | | | | 375 |
| ggc | ggc | acc | ttc | gcc | gcc | gga | ccg | cgt | cca | gag | ggc | ggc | ttc | gcg | gta | 2284 |
| Gly | Gly | Thr | Phe | Ala | Ala | Gly | Pro | Arg | Pro | Glu | Gly | Gly | Phe | Ala | Val |
| | | | 380 | | | | 385 | | | | 390 |
| cac | gcg | tcc | ctg | ccg | tac | gag | gag | aac | aca | tga | cccggcccgc | cgatccgccc | | | | 2337 |
| His | Ala | Ser | Leu | Pro | Tyr | Glu | Glu | Asn | Thr |
| | | 395 | | | | 400 |

| | | | |
|---|---|---|---|---|
| ggtgccccgg | tccgggtcct | catcgccgac | gaccaggcgc | tgctgcgcgg | cagcctgcgg | 2397 |
| gtgctcgtcg | acaccgagcc | cggcctggtg | gccacgtcgg | aggcggcgac | cggcacggag | 2457 |
| gcggtgcggt | tgcccggca | ggatccgccg | acgtggtcc | tgatggacgt | gcggatgccc | 2517 |
| gaaatggatg | gcatcgaggc | gacccggcag | atctgcggtt | ccccgagac | cgcggacgtc | 2577 |
| aaagtgctga | tcctgacgat | gttcgacctg | gacgagtacg | tctacgccgc | gctgcgggcc | 2637 |
| ggtgccagcg | gcttcctgct | gaaggacacg | ccgcccagcg | agttgctcgc | ggcggtacgg | 2697 |
| gtcatcgccg | ccggcgaggc | gctgctggca | ccggccgtga | cgcggcgcct | gatcgcggag | 2757 |
| ttcgtccacc | gcccggagcc | ctcgcgaccg | ctgcgtcgca | ccctggacgg | cgtgaccgag | 2817 |
| cgcgaacgtg | aagtcctcac | cctcatcgcc | tgcggcctgt | ccaacaccga | gatcgccgag | 2877 |
| cggctgtatc | tcggcattgc | caccgtgaag | acccacgtca | gccacctgct | caccaagctc | 2937 |
| gccacccgcg | atcgcgctca | gttggtgatc | gtcgcgtacg | agagcggcct | ggtcacggtg | 2997 |
| gcgcgaccac | cgatcggttc | ctgaggggcg | ccggcgcaca | cggtgcacgg | cctgggcggg | 3057 |
| gccgttcaga | atggatcacc | cgggtacacg | aggcgcagtt | cgtcgacatg | gctcatgagg | 3117 |
| tactcaccgg | ggcactgggt | ggatgccggg | gcccgggact | gcttcttgcg | cggctggtgg | 3177 |
| ccccagacgc | tgctgatgcc | gaagcggacg | gccaggacgt | ccacgaggac | gtcgagtgtt | 3237 |
| gtgagttgct | tgggcgtcgg | gtggtcgtag | cgtgcccact | ggttctgcca | gcgcggtccg | 3297 |
| aagtcgccgg | tgagcacgat | gccgagattg | ccggcgttga | agagttcagc | gtgtgagccc | 3357 |
| tcgatgccga | gtggccgccc | ctcgtagatc | gtcccggcgc | cgtcgatgat | gtagtggtaa | 3417 |
| ccgatgtcgg | ccttgtcgtc | cgcgaagtgc | gcccgctgga | tcgtgcgcgg | gccctcatgc | 3477 |
| gtgtacgtga | cggggtcggc | cgagtggtgg | atggtgatcc | agcggtagac | ggaggccagg | 3537 |
| ggccggttct | cgctgagcgg | tacgggactg | ccgcggtagg | gcggtggcgc | gagggggccg | 3597 |

-continued

```
gaggcggcct cgtggaaatc ccaggtacgc agcgggggt cgatctgcgg cggggccgcc    3657
ccccaggtgg cgcggccgac gacggacacg gtcagcggcc ctcgcggtgt catggcccac    3717
aactcgtagt cgccgctcgc cggatgcagg aagcgcgact cgtcccagca ggcggcgacg    3777
gggccgtgcg cggtgtcgac cggccgggtg ccgcaggacg tcagcctcag gggagtccgg    3837
tgcgggcgct gccccgagac cggcgcgttg aaccggccga tgtcggtgat cacggtggtg    3897
cggagttccg acaggtcgta gccgtcgcgg gggcattcga gggagcgcgg cggcggttcc    3957
acgaccctga gcgccgcatc gcaccggggg cagacgagaa cgagcacctc gcgggcgacc    4017
agctccgtcg tcgtaccggg cgggagccgg tggtggcggg gcagatcgag tggcgtgcgg    4077
ccgggccgca gttcggtcac gggcacgggg tcggtggctt cggcggcggg tgccagctcg    4137
tggtcggcgc aggcgaccgt ccaggcacgc gtcccggcgt cgggaaccat gagggtgccc    4197
agcgcgtccg tcgtggccgc gatcccggaa tgccgtcctc ccgatggcgg gatgagccgt    4257
acggtgaatc cggggatcgg gctgccgtcg cggcgcagga tcaccagggc cgtgtccgac    4317
ggtggtgaga gttcggcggc cagccccgcc tcgacgaagt gcagcaagcg gtgtgtcagt    4377
tgcagtacct cgggagagtc cggcgcgagc atggcctcgg cacggctgcg cacgctctcg    4437
aacgcgccgc cgagtgcgaa gcgcaggaag tcgacggcga acgcgacgat ctccccggcg    4497
acgaagccga ccgcggcgtc ggcgaagcga ggcgggccga agccaggtgc caggggggagc    4557
gccggcgctc cggcactggt cctggtggcg cgacgaacg cggtgcaacg ccggtccacg    4617
gcgccgtcgt agtactcacg cagctgcgcc gccagcgagc ggtgcgggtc gaaggactcg    4677
ccgaggttca ccccgtcgat gtcgcccagc agccgcggcg tcgaagcgtg gcgggcgacc    4737
cagtggtcca gcgaccgacc gcggtccgcg gccggcaccc cgggcgcgtg gcgggcgcgg    4797
acgtacgcgg cgagggcgcg cccgaggtca ccgctccagg tgagggcgag atccgctcga    4857
ggggccgggt ccagggggcc gggcgtctgc cggtcggccc cgtcgatgcc ggccagcacc    4917
tgcgccaggt cgagccgctc gaagccgtgc tgcacccgca gcagcgcggc cagccgggcg    4977
gcccggcggg gcagctccca ggacgagccc ggcgtctggt cgtacggggg gatgttccgc    5037
cggttctg                                                             5045
```

<210> SEQ ID NO 2
<211> LENGTH: 401
<212> TYPE: PRT
<213> ORGANISM: Streptomyces avermitilis

<400> SEQUENCE: 2

```
Val His Ala Gly Thr Ala Val Asp Pro Asp His Pro Ile Leu Ala
 1               5                  10                  15

Arg Arg Leu Ser Arg Arg Leu Ile Ala Leu Asp Gly Val Leu Val
                20                  25                  30

Phe Ala Tyr Ala Cys Ala Leu Leu Ser Thr Gly Pro Thr Gly Ile Ser
                35                  40                  45

Ser Ser Ser Ala Pro Pro Leu Pro Ala Pro Val Pro Trp Glu Arg Leu
            50                  55                  60

Val Leu Ile Ala Ala Ala Thr Ala Pro Val Ala Arg Arg Ile Trp
 65                 70                  75                  80

Pro Leu Pro Val Phe Ala Val Val Leu Ala Val Thr Ala Val Ala Val
                85                  90                  95

Val Arg Asp Ala Ala Trp Asp Pro Phe Leu Ser Ala Ala Phe Ala Leu
               100                 105                 110
```

```
Tyr Thr Val Ala Val Thr Val Pro Ser Arg His Trp Trp Gln Arg Trp
            115                 120                 125

Leu Pro Gly Leu Ala Ile Ala Leu Leu Thr Val Ala Gly Leu Ala Gly
130                 135                 140

Ala Ala Arg Ala Gly Glu Ala Phe Trp Trp Arg Gly Ser Pro Gly Leu
145                 150                 155                 160

Leu Leu Leu Gly Phe Ala Ala Leu Leu Gly Ala Trp Gln Leu Gly Arg
                165                 170                 175

Ala Ala Arg Gln Arg Arg Ala Phe Ala Val Arg Ala Ala Glu Gln Leu
            180                 185                 190

Ala Gln Arg Ala Val Thr Glu Glu Arg Leu Arg Ile Ala Arg Glu Leu
        195                 200                 205

His Asp Val Val Thr His Ser Met Gly Leu Ile Ala Val Lys Val Gly
    210                 215                 220

Val Ala Asn His Val Leu His Ile Arg Pro Gln Glu Ala Tyr Asp Ala
225                 230                 235                 240

Leu Gln Val Ile Glu Arg Thr Ser Arg Thr Ala Leu Asn Asp Met Arg
                245                 250                 255

Arg Met Leu Gly Val Leu Arg Thr Ser Glu Gly Glu Arg Gln Ser Ala
            260                 265                 270

Ala Leu Gly Pro Leu Pro Gly Ala Leu Ala Leu Pro Asp Leu Val Gly
        275                 280                 285

Gln Ala Gly Ala Gln Leu Thr Met Arg Gly Val Glu Ser Leu Pro Asp
    290                 295                 300

Gly Val Ala Leu Ala Val Tyr Arg Ile Val Gln Glu Ala Leu Thr Asn
305                 310                 315                 320

Val Ala Lys His Ala Gly Pro Glu Ala Arg Cys Arg Val Ala Val Asp
                325                 330                 335

Ala Asn Gly His Gly Val Arg Leu Glu Ile Thr Asp Asp Gly Gly Asp
            340                 345                 350

Arg Ser Pro Leu Ala Pro Lys Pro Gly Gly His Gly Ile Val Gly Met
        355                 360                 365

Arg Glu Arg Val Ala Leu Tyr Gly Gly Thr Phe Ala Ala Gly Pro Arg
    370                 375                 380

Pro Glu Gly Gly Phe Ala Val His Ala Ser Leu Pro Tyr Glu Glu Asn
385                 390                 395                 400

Thr

<210> SEQ ID NO 3
<211> LENGTH: 5045
<212> TYPE: DNA
<213> ORGANISM: Streptomyces avermitilis
<220> FEATURE:
<221> NAME/KEY: CDS
<222> LOCATION: (2314)..(3021)
<223> OTHER INFORMATION: aveR2 ORF

<400> SEQUENCE: 3
cgagttgctg gtcatcggcg tactcctccc ggcgactccg cccggtactc gaccgcggca      60
gcggtcagcc gcatgaacgc ctcttcgaga gacacggtct tccgcgtcac ctcgtgcacc     120
gtcacggcgt gcgccgcgac gagttcgccg atccgctccg cggcggcggc caccttcagg     180
ctgccgtcgg agcagtcggt gaccgtgatt cccgcgccga ccagcacgtc gcgcagccgc     240
cgcggttccg gagtgcgcac ccgcaccccc acgtccgtgt acctgtcgat gaactcgctc     300
```

-continued

```
atgctggtgt ccgcgaggag ccgaccgcgg ccgatgatga cgaggtggtc cacggtgagc    360
gccgcctcgc tcatcagatg gctggacacg aagacggtgc gtccctgtgc cgccaggtcc    420
cgcatgaggt gccgcagcca caggacgcct tccgggtcga gcccgttgac cggctcgtcg    480
agcaccagga cggcggggtc gccgagcagc gccgcggcga ttcccagccg ctgactcatg    540
cccagcgaga acgtccccgc cgccggcgc acggcgctcc gcaggcccgc cagctcgatc     600
acctcacgga cgcggcgggg cgggatccgg ttgctgcggg ccagccagcg caagtggttc    660
agcgcggttc ggccggggtg caccgccctg cgtcgagca gtgcccccac cgtccgcagc     720
gggtcgcgga ccgctggta gggcgcgccg tcgatgcgta cctcgccggc cgtcgggcgg     780
tccaggccca gcatcatgcg catcgcgtg gacttcccgg cgccgttggg gccaaggaat     840
ccggtcaccc gaccggtccg tacctggaag gtaagaccct ccacaacggt ggtggtcccg    900
tagcgcttgg tcaggtccgt gacttcgatc atgccggtga tggtccgtga cgacaggctc    960
ccgccgcgtc ccgctcgggg ctgactgccc cttctccacc cccggttgga gaatgaccgc   1020
cacccgcggc cgcgcatcag gctgcaggag gagcggcttt gaccaccgct ggacggaggc   1080
ggagcggcgt acgcctggat atggtcgagc ggtgcatgca ggtaccgcgg tggaccccga   1140
cgaccatccg atcctggccc ggcgactgag ccggcgccga ctcatcgccc tggacggcgt   1200
gctcgtattc gcctacgcat gcgcgctgct gtcgaccggg ccgacaggca tctcgtcgtc   1260
gtccgcgccg ccgctcccgg ccccggtgcc gtgggagcgg ctcgtgctca tcgccgcggc   1320
cactgcgcct gtcgccgtac ggcggatctg ccgttgccc gtgttcgcgg tcgtgctggc    1380
ggtgaccgcc gtggccgtcg tgcgggacgc ggcgtgggac ccgttcctgt cggcggcgtt   1440
cgccctctac accgtcgccg tcacggtgcc ctcgcgccac tggtggcaac gctggttacc   1500
cggcctggcg atcgctttgc tgaccgtggc cggccttgcc ggagcagcgc gtgccggcga   1560
ggccttctgg tggcgcggca gccccggtct gctgctgctc ggcttcgccg cactgctcgg   1620
cgcctggcaa ctgggacgcg ccgcgcggca gaggcgcgca ttcgccgtcc gggcggccga   1680
gcagctcgca caacgggccg tcacggagga acgcctgcgg atagcccgcg aactgcatga   1740
cgtcgtcacg cacagcatgg gcctgatcgc ggtcaaggtc ggcgtcgcca accacgtgtt   1800
gcacatcagg ccgcaggagg cgtacgacgc gctccaggtc atcgaacgca cgagccgcac   1860
cgcgctgaac gacatgcgcc ggatgctcgg tgtgctgcgt acgtccgagg gtgagcggca   1920
gtcagcggct ctcggcccgc tgcctggcgc ccttgctctc cctgacctcg tcgggcaggc   1980
cggcgcgcag ctgactatgc gcggtgtcga gagtctgccc gacggagtcg cgctggccgt   2040
ctaccggatc gtgcaggagg cgctcaccaa tgtcgccaag cacgccggcc ggaggcccg    2100
ctgccgggtg gcggtcgatg cgaacggcca cggcgtccgg ctcgagataa ccgacgacgg   2160
aggcgaccgg agcccctcg cgccgaagcc cggcggccac ggaatcgtcg gcatgcgcga   2220
acgcgtcgcc ctgtacggcg gcaccttcgc cgccggaccg cgtccagagg gcggcttcgc   2280
ggtacacgcg tccctgccgt acgaggagaa cac atg acc cgg ccc gcc gat ccg   2334
                                     Met Thr Arg Pro Ala Asp Pro
                                      1               5 ccc ggt gcc ccg gtc cgg gtc ctc atc gcc gac gac cag gcg ctg ctg    2382
Pro Gly Ala Pro Val Arg Val Leu Ile Ala Asp Asp Gln Ala Leu Leu
        10              15                  20 cgc ggc agc ctg cgg gtg ctc gtc gac acc gag ccc ggc ctg gtg gcc    2430
Arg Gly Ser Leu Arg Val Leu Val Asp Thr Glu Pro Gly Leu Val Ala
    25              30                  35 acg tcg gag gcg gcg acc ggc acg gag gcg gtg cgg ctt gcc cgg cag    2478
```

-continued

```
Thr Ser Glu Ala Ala Thr Gly Thr Glu Ala Val Arg Leu Ala Arg Gln
 40                  45                  50                  55 gat ccg ccg gac gtg gtc ctg atg gac gtg cgg atg ccc gaa atg gat    2526
Asp Pro Pro Asp Val Val Leu Met Asp Val Arg Met Pro Glu Met Asp
                 60                  65                  70 ggc atc gag gcg acc cgg cag atc tgc ggt tcc ccc gag acc gcg gac    2574
Gly Ile Glu Ala Thr Arg Gln Ile Cys Gly Ser Pro Glu Thr Ala Asp
             75                  80                  85 gtc aaa gtg ctg atc ctg acg atg ttc gac ctg gac gag tac gtc tac    2622
Val Lys Val Leu Ile Leu Thr Met Phe Asp Leu Asp Glu Tyr Val Tyr
         90                  95                 100 gcc gcg ctg cgg gcc ggt gcc agc ggc ttc ctg ctg aag gac acg ccg    2670
Ala Ala Leu Arg Ala Gly Ala Ser Gly Phe Leu Leu Lys Asp Thr Pro
     105                 110                 115 ccc agc gag ttg ctc gcg gcg gta cgg gtc atc gcc gcc ggc gag gcg    2718
Pro Ser Glu Leu Leu Ala Ala Val Arg Val Ile Ala Ala Gly Glu Ala
120                 125                 130                 135 ctg ctg gca ccg gcc gtg acg cgg cgc ctg atc gcg gag ttc gtc cac    2766
Leu Leu Ala Pro Ala Val Thr Arg Arg Leu Ile Ala Glu Phe Val His
                140                 145                 150 cgc ccg gag ccc tcg cga ccg ctg cgt cgc acc ctg gac ggc gtg acc    2814
Arg Pro Glu Pro Ser Arg Pro Leu Arg Arg Thr Leu Asp Gly Val Thr
            155                 160                 165 gag cgc gaa cgt gaa gtc ctc acc ctc atc gcc tgc ggc ctg tcc aac    2862
Glu Arg Glu Arg Glu Val Leu Thr Leu Ile Ala Cys Gly Leu Ser Asn
        170                 175                 180 acc gag atc gcc gag cgg ctg tat ctc ggc att gcc acc gtg aag acc    2910
Thr Glu Ile Ala Glu Arg Leu Tyr Leu Gly Ile Ala Thr Val Lys Thr
    185                 190                 195 cac gtc agc cac ctg ctc acc aag ctc gcc acc cgc gat cgc gct cag    2958
His Val Ser His Leu Leu Thr Lys Leu Ala Thr Arg Asp Arg Ala Gln
200                 205                 210                 215 ttg gtg atc gtc gcg tac gag agc ggc ctg gtc acg gtg gcg cga cca    3006
Leu Val Ile Val Ala Tyr Glu Ser Gly Leu Val Thr Val Ala Arg Pro
                220                 225                 230 ccg atc ggt tcc tga ggggcgccgg cgcacacggt gcacggcctg ggcggggccg    3061
Pro Ile Gly Ser
            235 ttcagaatgg atcacccggg tacacgaggc gcagttcgtc gacatggctc atgaggtact    3121 caccggggca ctgggtggat gccgggggccc gggactgctt cttgcgcggc tggtggcccc    3181 agacgctgct gatgccgaag cggacggcca ggacgtccac gaggacgtcg agtgttgtga    3241 gttgcttggg cgtcgggtgg tcgtagcgtc cccactggtt ctgccagcgc ggtccgaagt    3301 cgccggtgag cacgatgccg agattgccgg cgttgaagag ttcagcgtgt gagccctcga    3361 tgccgagtgg ccgcccctcg tagatcgtcc cggcgccgtc gatgatgtag tggtaaccga    3421 tgtcggcctt gtcgtccgcg aagtgcgccc gctggatcgt gcgcgggccc tcatgcgtgt    3481 acgtgacggg gtcggccgag tggtggatgg tgatccagcg gtagacggag gccaggggcc    3541 ggttctcgct gagcggtacg ggactgccgc ggtaggcgg tggcgcgagg gggccggagg    3601 cggcctcgtg gaaatcccag gtacgcagcg ggggtcgat ctgcggcggg gccgcccccc    3661 aggtggcgcg gccgacgacg gacacggtca gcggccctcg cggtgtcatg gcccacaact    3721 cgtagtcgcc gctcgccgga tgcaggaagc gcgactcgtc ccagcaggcg gcgacggggc    3781 cgtgcgcggt gtcgaccggc cggtgccgcg aggacgtcag cctcagggga gtccggtgcg    3841 ggcgctgccc cgagaccggc gcgttgaacc ggccgatgtc ggtgatcacg gtggtgcgga    3901
```

-continued

```
gttccgacag tcgtagccg tcgcggggc attcgaggga gcgcggcggc ggttccacga      3961
ccctgagcgc cgcatcgcac cgggggcaga cgagaacgag cacctcgcgg gcgaccagct      4021
ccgtcgtcgt accgggcggg agccggtggt ggcggggcag atcgagtggc gtgcggccgg      4081
gccgcagttc ggtcacgggc acgggtcgg tggcttcggc ggcgggtgcc agctcgtggt      4141
cggcgcaggc gaccgtccag gcacgcgtcc cggcgtcggg aaccatgagg gtgcccagcg      4201
cgtccgtcgt ggccgcgatc ccggaatgcc gtcctcccga tggcgggatg agccgtacgg      4261
tgaatccggg gatcgggctg ccgtcgcggc gcaggatcac cagggccgtg tccgacggtg      4321
gtgagagttc ggcggccagc cccgcctcga cgaagtgcag caagcggtgt gtcagttgca      4381
gtacctcggg agagtccggc gcgagcatgg cctcggcacg gctgcgcacg ctctcgaacg      4441
cgccgccgag tgcgaagcgc aggaagtcga cggcgaacgc gacgatctcc ccggcgacga      4501
agccgaccgc ggcgtcggcg aagcgaggcg ggccgaagcc aggtgccagg gggagcgccg      4561
gcgctccggc actggtcctg gtggcggcga cgaacgcggt gcaacgccgg tccacggcgc      4621
cgtcgtagta ctcacgcagc tgcgccgcca gcgagcggtg cgggtcgaag gactcgccga      4681
ggttcacccc gtcgatgtcg cccagcagcc gcggcgtcga agcgtggcgg gcgacccagt      4741
ggtccagcga ccgaccgcgg tccgcggccg gcaccccggg cgcgtggcgg gcgcggacgt      4801
acgcggcgag ggcgcgcccg aggtcaccgc tccaggtgag ggcgagatcc gctcgagggg      4861
ccgggtccag ggggccgggc gtctgccggt cggccccgtc gatgccggcc agcacctgcg      4921
ccaggtcgag ccgctcgaag ccgtgctgca cccgcagcag cgcggccagc cgggcggccc      4981
ggcggggcag ctcccaggac gagcccggcg tctggtcgta cgggggatg ttccgccggt      5041 tctg                                                                  5045
```

<210> SEQ ID NO 4
<211> LENGTH: 235
<212> TYPE: PRT
<213> ORGANISM: Streptomyces avermitilis

<400> SEQUENCE: 4

```
Met Thr Arg Pro Ala Asp Pro Pro Gly Ala Pro Val Arg Val Leu Ile
  1               5                  10                  15

Ala Asp Asp Gln Ala Leu Leu Arg Gly Ser Leu Arg Val Leu Val Asp
                 20                  25                  30

Thr Glu Pro Gly Leu Val Ala Thr Ser Glu Ala Ala Thr Gly Thr Glu
             35                  40                  45

Ala Val Arg Leu Ala Arg Gln Asp Pro Pro Asp Val Leu Met Asp
         50                  55                  60

Val Arg Met Pro Glu Met Asp Gly Ile Glu Ala Thr Arg Gln Ile Cys
 65                  70                  75                  80

Gly Ser Pro Glu Thr Ala Asp Val Lys Val Leu Ile Leu Thr Met Phe
                 85                  90                  95

Asp Leu Asp Glu Tyr Val Tyr Ala Ala Leu Arg Ala Gly Ala Ser Gly
                100                 105                 110

Phe Leu Leu Lys Asp Thr Pro Pro Ser Glu Leu Leu Ala Ala Val Arg
            115                 120                 125

Val Ile Ala Ala Gly Glu Ala Leu Leu Ala Pro Val Thr Arg Arg
        130                 135                 140

Leu Ile Ala Glu Phe Val His Arg Pro Glu Pro Ser Arg Pro Leu Arg
145                 150                 155                 160

Arg Thr Leu Asp Gly Val Thr Glu Arg Glu Arg Glu Val Leu Thr Leu
```

```
                       165                 170                 175

Ile Ala Cys Gly Leu Ser Asn Thr Glu Ile Ala Glu Arg Leu Tyr Leu
                180                 185                 190

Gly Ile Ala Thr Val Lys Thr His Val Ser His Leu Leu Thr Lys Leu
            195                 200                 205

Ala Thr Arg Asp Arg Ala Gln Leu Val Ile Val Ala Tyr Glu Ser Gly
        210                 215                 220

Leu Val Thr Val Ala Arg Pro Pro Ile Gly Ser
225                 230                 235

<210> SEQ ID NO 5
<211> LENGTH: 394
<212> TYPE: PRT
<213> ORGANISM: Streptomyces coelicolor

<400> SEQUENCE: 5

Met His Arg Trp Gln Ala Val Arg Arg Ile Glu Ser Leu Val Arg
 1               5                  10                  15

Val Leu Gly Ser Glu Arg Pro Phe Thr Arg Arg Ala Asp Leu Val Leu
            20                  25                  30

Leu Leu Val Leu Leu Val Pro Ser Ala Phe Ala Thr Gly Thr Leu Glu
        35                  40                  45

Thr Ala Pro Val Ala Trp Leu Thr Ala Cys Leu Leu Ile Ala Ala Ala
     50                  55                  60

Val Val Val Gln Arg Thr Ala Pro Leu Leu Ser Leu Leu Ala Ala
 65                  70                  75                  80

Leu Leu Thr Leu Phe Tyr Pro Trp Phe Gly Ala Asn Leu Trp Pro Ser
                85                  90                  95

Met Ala Thr Val Val Leu Ser Cys Leu Ala Gly Arg Leu Thr Arg
            100                 105                 110

Leu Trp Pro Ala His Leu Val Phe Leu Cys Val Ala Ala Gly Leu
        115                 120                 125

Leu Leu Val Ala Thr Val Gly Gln Gly Lys Asp Trp Leu Ser Leu Leu
    130                 135                 140

Met Thr Glu Phe Val Ala Cys Val Leu Pro Trp Trp Ala Gly Asn Trp
145                 150                 155                 160

Trp Ser Gln Arg Thr Ala Leu Thr His Ala Gly Trp Glu His Ala Glu
                165                 170                 175

Gln Leu Glu Trp Arg Gln Arg Tyr Ile Ala Asp Gln Ala Arg Met Lys
            180                 185                 190

Glu Arg Ala Arg Ile Ala Gln Asp Ile His Asp Ser Leu Gly His Glu
        195                 200                 205

Leu Ser Val Met Ala Leu Leu Ala Gly Gly Leu Glu Leu Ala Pro Gly
    210                 215                 220

Leu Ser Asp Pro His Arg Glu Ser Val Gly Gln Leu Arg Glu Arg Cys
225                 230                 235                 240

Thr Met Ala Thr Glu Arg Leu His Glu Val Ile Gly Leu Leu Arg Glu
                245                 250                 255

Asp Pro Asn Pro Ser Leu Thr Pro Ala Asp Glu Ser Val Ala Gln Leu
            260                 265                 270

Val Arg Arg Phe Gln Arg Ser Gly Thr Pro Val Arg Phe Gln Glu Asp
        275                 280                 285

Gly Ala Arg Asp Arg Pro Gly Thr Pro Leu Leu Ser Asp Leu Ala Ala
    290                 295                 300
```

-continued

```
Tyr Arg Val Val Gln Glu Ala Leu Thr Asn Ala Ala Lys His Ala Pro
305                 310                 315                 320

Gly Ala Pro Ile Asp Val Arg Val Thr His Thr Ala Asp Glu Thr Val
                325                 330                 335

Val Ser Val Val Asn Glu Arg Pro Glu Arg Gly Gly Ser Val Pro Ala
                340                 345                 350

Ala Gly Ser Gly Ser Gly Leu Ile Gly Leu Asp Glu Arg Val Arg Leu
            355                 360                 365

Ala Gly Gly Thr Leu Arg Thr Gly Pro Arg Ala Gly Gly Phe Glu Val
        370                 375                 380

Tyr Ala Arg Leu Pro Arg Gly Ala Ser Ser
385                 390

<210> SEQ ID NO 6
<211> LENGTH: 222
<212> TYPE: PRT
<213> ORGANISM: Streptomyces coelicolor

<400> SEQUENCE: 6

Met Ile Arg Val Leu Leu Ala Asp Asp Glu Thr Ile Ile Arg Ala Gly
 1               5                  10                  15

Val Arg Ser Ile Leu Thr Thr Glu Pro Gly Ile Glu Val Val Ala Glu
                20                  25                  30

Ala Ser Asp Gly Arg Glu Ala Val Glu Leu Ala Arg Lys His Arg Pro
            35                  40                  45

Asp Val Ala Leu Leu Asp Ile Arg Met Pro Glu Met Asp Gly Leu Thr
        50                  55                  60

Ala Ala Gly Glu Met Arg Thr Thr Asn Pro Asp Thr Ala Val Val Val
65                  70                  75                  80

Leu Thr Thr Phe Gly Glu Asp Arg Tyr Ile Glu Arg Ala Leu Asp Gln
                85                  90                  95

Gly Val Ala Gly Phe Leu Leu Lys Ala Ser Asp Pro Arg Asp Leu Ile
                100                 105                 110

Ser Gly Val Arg Ala Val Ala Ser Gly Gly Ser Cys Leu Ser Pro Leu
            115                 120                 125

Val Ala Arg Arg Leu Met Thr Glu Leu Arg Arg Ala Pro Ser Pro Arg
        130                 135                 140

Ser Glu Val Ser Gly Glu Arg Thr Thr Leu Leu Thr Lys Arg Glu Gln
145                 150                 155                 160

Glu Val Leu Gly Met Leu Gly Ala Gly Leu Ser Asn Ala Glu Ile Ala
                165                 170                 175

Gln Arg Leu His Leu Val Glu Gly Thr Ile Lys Thr Tyr Val Ser Ala
                180                 185                 190

Ile Phe Thr Gln Leu Glu Val Arg Asn Arg Val Gln Ala Ala Ile Ile
            195                 200                 205

Ala Tyr Glu Ala Gly Leu Val Lys Asp Ala Asp Leu Asn Arg
        210                 215                 220
```